(12) United States Patent
Case et al.

(10) Patent No.: US 6,599,692 B1
(45) Date of Patent: Jul. 29, 2003

(54) FUNCTIONAL GENOMICS USING ZINC FINGER PROTEINS

(75) Inventors: Casey C. Case, San Mateo; Lei Zhang, San Francisco, both of CA (US)

(73) Assignee: Sangamo BioScience, Inc., Richmond, CA (US)

( * ) Notice: Subject to any disclaimer, the term of this patent is extended or adjusted under 35 U.S.C. 154(b) by 0 days.

(21) Appl. No.: 09/395,448

(22) Filed: Sep. 14, 1999

(51) Int. Cl.[7] .................. C12Q 1/02; C12Q 1/68; C12N 15/12
(52) U.S. Cl. .................. 435/4; 435/6; 536/23.1
(58) Field of Search .................. 435/4, 6, 320.1, 435/69.1; 536/23.1, 23.4

(56) References Cited

U.S. PATENT DOCUMENTS

| | | |
|---|---|---|
| 4,990,607 A | 2/1991 | Katagiri et al. |
| 5,096,814 A | 3/1992 | Aivasidis et al. |
| 5,096,815 A | 3/1992 | Ladner et al. |
| 5,198,346 A | 3/1993 | Ladner et al. |
| 5,223,409 A | 6/1993 | Ladner et al. |
| 5,243,041 A | 9/1993 | Fernandez-Pol |
| 5,302,519 A | 4/1994 | Blackwood et al. |
| 5,324,638 A | 6/1994 | Tao et al. |
| 5,324,818 A | 6/1994 | Nabel et al. |
| 5,324,819 A | 6/1994 | Oppermann et al. |
| 5,340,739 A | 8/1994 | Stevens et al. |
| 5,348,864 A | 9/1994 | Barbacid |
| 5,350,840 A | 9/1994 | Call et al. |
| 5,356,802 A | 10/1994 | Chandrasegaran |
| 5,376,530 A | 12/1994 | De The et al. |
| 5,403,484 A | 4/1995 | Ladner et al. |
| 5,436,150 A | 7/1995 | Chandrasegaran |
| 5,487,994 A | 1/1996 | Chandrasegaran |
| 5,498,530 A | 3/1996 | Schatz et al. |
| 5,578,483 A | 11/1996 | Evans et al. |
| 5,597,693 A | 1/1997 | Evans et al. |
| 5,639,592 A | 6/1997 | Evans et al. |
| 5,674,738 A | 10/1997 | Abramson et al. |
| 5,702,914 A | 12/1997 | Evans et al. |
| 5,789,538 A | 8/1998 | Rebar et al. |
| 5,792,640 A | 8/1998 | Chandrasegaran |
| 5,869,618 A | 2/1999 | Lippman et al. |
| 5,871,902 A | 2/1999 | Weininger et al. |
| 5,871,907 A | 2/1999 | Winter et al. |
| 5,916,794 A | 6/1999 | Chandrasegaran |
| 5,939,538 A * | 8/1999 | Leavitt et al. ............. 536/23.1 |
| 5,972,615 A | 10/1999 | An et al. |
| 6,001,885 A | 12/1999 | Vega et al. |
| 6,007,988 A | 12/1999 | Choo et al. |
| 6,013,453 A | 1/2000 | Choo et al. |

FOREIGN PATENT DOCUMENTS

| | | |
|---|---|---|
| WO | WO 95/19431 | 7/1995 |
| WO | WO 96/06110 | 2/1996 |
| WO | WO 96/06166 | 2/1996 |
| WO | WO 96/11267 | 4/1996 |
| WO | WO 96/20951 | 7/1996 |
| WO | WO 96/32475 | 10/1996 |
| WO | WO 97/27212 | 7/1997 |
| WO | WO 97/27213 | 7/1997 |
| WO | WO 98/53057 | 11/1998 |
| WO | WO 98/53058 | 11/1998 |
| WO | WO 98/53059 | 11/1998 |
| WO | WO 98/53060 | 11/1998 |
| WO | WO 98/54311 | 12/1998 |
| WO | WO 99/35494 | 7/1999 |
| WO | WO 99/36553 | 7/1999 |
| WO | WO 99/41371 | 8/1999 |
| WO | WO 99/42474 | 8/1999 |
| WO | WO 99/45132 | 9/1999 |
| WO | WO 99/47656 | 9/1999 |
| WO | WO 99/48909 | 9/1999 |
| WO | WO 00/23464 | 4/2000 |
| WO | WO 00/27878 | 5/2000 |
| WO | WO 00/41566 | 7/2000 |

OTHER PUBLICATIONS

Beerli etal., "Toward controlling gene expressing at will: Specific regulation of the erbB–2/HER–2 promoter by using polydactyl zinc finger proteins constructed from molecular building blocks" Proc. Natl. Acad. Sci. USA vol. 95, pp. 14628–14633, 1998.*

Gossen et al., "Tight control of gene expression in mammalian cells by tetracycline–responsive promoters" Proc. Natl. Acad. Sci. USA vol. 89, pp. 5547–5551, 1992.*

Beerli et al., "Positive and negative regulation of endogeneous genes by designed transcription factors" PNAS USA, vol. 97, 1495–1500, 2000.*

Margolin et al., "Kruppel–associated boxes are potent transcriptional repression domains" PNAS USA vol. 91, 4509–4513, 1994.*

Holstege et al., "Transcriptional regulation: contending with complexity" PNAS USA vol. 96, 2–4, 1999.*

Gossen et al., "Tight control of gene expression in mammalian cells by tetracycline–responsive promoters" Proc. Natl. Acad. Sci. USA vol. 89, pp. 5547–5551, 1992.*

King et al., A Dictionary of Genetics, Fifth Edition, New York, Oxford, Oxford University Press, 1997, p. 136.*

Imhof et al., "Transcriptional Regulation of the AP–Zalpha Promotor by BTEB–1 and AP–ZREP, a Novel WT–1/EGR–Related Zinc Finger Repressor," *Molecular and Cellular Biology* 19(1):194–204 (1999).

Liu et al., "Transcription Factor EGR–1 Suppresses the Growth and Transformation of Human HT–1080 Fibrosarcoma Cells by Induction of Transforming Growth Factor Beta 1," *Proceedings of the National Academy of Sciences of USA, US, National Academy of Science, Washington* 93(21):11831–11836 (1996).

(List continued on next page.)

Primary Examiner—John S. Brusca
(74) Attorney, Agent, or Firm—Robins & Pasternak LLP

(57) ABSTRACT

The present invention provides methods of regulating gene expression using recombinant zinc finger proteins, for functional genomics and target validation applications.

55 Claims, 5 Drawing Sheets

OTHER PUBLICATIONS

Spengler et al., "Regulation of Apoptosis and Cell Cycle Arrest by ZZC1 A Novel ZincFinger Protein Expressed in the Pituitary Gland and the Brain," *EMBO Journal 6B, Oxford University Press, Surrey* 16(10):2814–2825 (1997).

Corbi et al., "Synthesis of a New Zinc Finger Peptide; Comparison of Its 'Code' Deduced and 'CASTing' Derived Binding Sites," *FEBS Letters*, 417:71–74 (1997).

Wang et al., "Dimerization of Zinc Fingers Mediated by Peptides Evolved In Vitro from Random Sequences," *Proc. Natl. Acad. Sci. USA*, 96:9568–9573 (1999).

Wolfe et al., "Analysis of Zinc Fingers Optimized Via Phage Display: Evaluating the Utility of a Recognition Code," *J. Mol. Biol.*, 285:1917–1934 (1999).

Klug, "Zinc Finger Peptides for the Regulation of Gene Expression," *J. Mol. Biol.*, 293:215–218 (1999).

Kang et al., "Zinc Finger Proteins as Designer Transcription Factors," *J. Biol. Chem.*, 275(12):8742–8748 (2000).

Hamilton et al., "Comparison of the DNA Binding Characteristics of the Related Zinc Finger Proteins WT1 and EGR1," *Biochemistry*, 37:2051–2058 (1998).

Kriwacki et al., "Sequence–Specific Recognition of DNA by Zinc–Finger Peptides Derived from the Transcription Factor Sp1," *Proc. Natl. Acad. Sci. USA*, 89:9759–9763 (1992).

Nakagama et al., "Sequence and Structural Requirements for High–Affinity DNA Binding by the WT1 Gene Product," *Molecular and Cellular Biology*, 15(3):1489–1498 (1995).

Skerka et al., "Coordinate Expression and Distinct DNA–Binding Characteristics of the Four EGR–Zinc Finger Proteins in Jurkat T Lymphocytes," *Immunobiology*, 198:179–191 (1997).

Kothekar, "Computer Simulation of Zinc Finger Motifs from Cellular Nucleic Acid Binding Proteins and their Interaction with Consensus DNA Sequences," *FEBS Letters*, 274(1,2):217–222 (1990).

Agarwal et al., "Stimulation of Transcript Elongation Requires both the Zinc Finger and RNA Polymerase II Binding Domains of Human TFIIS," *Biochemistry*, 30(31):7842–7851 (1991).

Antao et al., "A thermodynamic study of unusually stable RNA and DNA hairpins," *Nuc. Acids. Res.*, 19(21):5901–5905 (1991).

Barbas, C. F., "Recent advances in phage display," *Curr. Opin. Biotech.*, 4:526–530 (1993).

Barbas et al., "Assembly of combinatorial antibody libraries on phage surfaces: The gene III site," *PNAS*, 88:7978–7982 (1991).

Barbas et al, "Semisynthetic combinatorial antibody libraries: A chemical solution to the diversity problem," *PNAS*, 89:4457–4461 (1992).

Bellefroid et al., "Clustered organization of homologous KRAB zinc–finger genes with enhanced expression in human T lymphoid cells," *EMBO J.*, 12(4):1363–1374 (1993).

Berg, J. M., "DNA Binding Specificity of Steroid Receptors," *Cell*, 57:1065–1068 (1989).

Berg, J. M., "Sp1 and the subfamily of zinc finger proteins with guanine–rich binding sites," *PNAS*, 89:11109–11110 (1992).

Berg et al., "The Galvanization of Biology: A Growing Appreciation for the Roles of Zinc," *Science*, 271:1081–1085 (1996).

Bergqvist et al., "Loss of DNA–binding and new transcriptional trans–activation function in polyomavirus large T–antigen with mutation of zinc finger motif," *Nuc. Acids Res.*, 18(9):2715–2720 (1990).

Blaese et al., "Vectors in cancer therapy: how will they deliver?," *Cancer Gene Therapy*, 2(4):291–297 (1995).

Caponigro et al., "Transdominant genetic analysis of a growth control pathway," *PNAS*, 95:7508–7513 (1998).

Celenza et al., "A Yeast Gene That Is Essential for Release from Glucose Repression Encodes a Protein Kinase," *Science*, 233:1175–1180 (1986).

Cheng et al., "Identification of Potential Target Genes for Adr1p through Characterization of Essential Nucleotides in UAS1," *Mol. Cellular Biol.*, 14(6):3842–3852 (1994).

Cheng et al., "A Single Amino Acid substitution in Zinc Finger 2 of Adr1p Changes its Binding Specificity at two Positions in UAS1," *J. Mol. Biol.*, 251:1–8 (1995).

Choo et al., "A role in DNA binding for the linker sequences of the first three zinc fingers of TFIIIA," *Nuc. Acids Res.*, 21(15):3341–3346 (1993).

Choo et al., "Designing DNA–binding proteins on the surface of filamentous phage," *Curr. Opin. Biotechnology*, 6:431–436 (1995).

Choo et al., "Promoter–specific Activation of Gene Expression Directed by Bacteriophage–selected Zinc Fingers," *J. Mol. Biol.*, 273:525–532 (1997).

Choo, Y., "Recognition of DNA methylation by zinc fingers," *Nature Struct. Biol.*, 5(4):264–265 (1998).

Choo et al., "All wrapped up," *Nature Structural Biology*, 5(4):253–255 (1998).

Choo, Y., "End effects in DNA recognition by zinc finger arrays," *Nuc. Acids Res.*, 26(2):554–557 (1998).

Choo et al., "Physical basis of a protein–DNA recognition code," *Curr. Opin. Struct. Biol.*, 7(1):117–125 (1997).

Choo et al., "Toward a code for the interactions of zinc fingers with DNA: Selection of randomized fingers displayed on phage," *PNAS*, 91:11163–11167 (1994).

Choo et al., "Selection of DNA binding sites for zinc fingers using rationally randomized DNA reveals coded interacitons," *PNAS*, 91:11168–11172 (1994).

Clarke et al., "Zinc Finger in *Caenorhabditis elegans*: Finding Families and Probing Pathways," *Science*, 282:2018–2022 (1998).

Crozatier et al., "Single Amino Acid Exchanges in Separate Domains of the Drosophila serendipity δ Zinc Finger Protein Cause Embryonic and Sex Baised Lethality," *Genetics*, 131:905–916 (1992).

Debs et al., "Regulation of Gene Expression in Vivo by Liposome–mediated Delivery of a Purified Transcription Factor*," *J. Biological Chemistry*, 265(18):10189–10192 (1990).

Desjarlais et al., "Length–encoded multiplex binding site determination: Application to zinc finger proteins," *PNAS*, 91:11099–11103 (1994).

Desjarlais et al., "Use of a zinc–finger consensus sequence framework and specificity rules to design specific DNA binding proteins," *PNAS*, 90:2256–2260 (1993).

Desjarlais et al., "Toward rules relating zinc finger protein sequences and DNA binding site preferences," *PNAS*, 89(16):7345–7349 (1992).

Desjarlais et al., "Redesigning the DNA–Binding Specificity of a Zinc Finger Protein: A Data Base–Guided Approach," *Proteins: Structure, Function, and Genetics*, 12(2):101–104 (1992).

Desjarlais et al., "Redesigning the DNA–Binding Sepcificity of a Zinc Finger Protein: A Data Base–Guided Approach," *Proteins: Structure, Function, and Genetics*, 13(3):272 (1992).

DiBello et al., "The Drosophila Broad–ComplexEncodes a Family of Related Proteins Contianing Zinc Fingers," *Genetics*, 129:385–397 (1991).

Elrod–Erickson et al., "High–resolution structures of variant Zif268–DNA complexes: implications for understanding zinc finger–DNA recognition," *Structure*, 6(4):451–464 (1988).

Elrod–Erickson et al., "Zif268 protein–DNA complex refined at 1.6 Å: a model system for understanding zinc finger–DNA interactions," *Structure*, 4(10):1171–1180 (1996).

Fairall et al., "The crystal structure of a two zinc–finger peptide reveals an extension to the rules for zinc–finger/DNA recognition," *Nature*, 366:483–487 (1993).

Frankel et al., "Fingering Too Many Proteins," *Cell*, 53:675 (1988).

Friesen et al., "Phage Display of RNA Binding Zinc Fingers from Transcription Factor IIIA*," *J. Biological Chem.*, 272(17):10994–10997 (1997).

Friesen et al., "Specific RNA binding proteins constructed from zinc fingers," *Nature Structural Biology*, 5(7):543–546(1998).

Gogos et al., "Recognition of diverse sequences by class I zinc fingers: Asymmetries and indirect effects on specificity in the interaction between CF2II and A+T–rich sequence elements," *PNAS*, 93(5):2159–2164 (1996).

Gossen et al., "Tight control of gene expression in mammalian cells by tetracycline–responsive promoters," *PNAS*, 89:5547–5551 (1992).

Greisman et al., "A General Strategy for Selecting High–Affinity Zinc Finger Proteins for Diverse DNA Target Sites," *Science*, 275:657–661 (1997).

Hamilton et al., "High Affinity binding sites for the Wilms' tumor suppressor protein WT1," *Nuc. Acids Res.*, 23(2):277–284 (1995).

Hanas et al., "Internal delection mutants of Xenopus transcription factor IIIA," *Nuc. Acids Res.*, 17(23):9861–9870 (1989).

Hayes et al., "Locations of Contacts between Individual Zinc Fingers of *Xenopus laevis* Transcription Factor IIIA and the Internal Control Region of a 5S RNA Gene," *Biochemistry*, 31:11600–11605 (1992).

Heinzel et al., "A complex containing N–CoR, mSin3 and histone deacetylase mediated transcriptional repression," *Nature*, 387:43–48 (1997).

Hirst et al., "Discrimination of DNA response elements for thyroid hormone and estrogen is dependant on dimerization of receptor DNA binding domains," *PNAS*, 89:5527–5531 (1992).

Hoffman et al., "Structures of DNA–binding mutant zinc finger domains: Implications for DNA binding," *Protein Science*, 2:951–965 (1993).

Islan et al., "Synergy between adjacent zinc fingers in sequence–specific DNA recognition," *PNAS*, 94(11):5617–5621 (1997).

Islan et al., "Comprehensive DNA Recognition through Concerted Interactions from Adjacent Zinc Fingers," *Biochemistry*, 37:12026–12033 (1998).

Jacobs, G. H., "Determination of the base recognition positions of zinc fingers from sequence analysis," *EMBO J.*, 11(12):4507–4517 (1992).

Jamieson et al., "A zinc finger director for high–affinity DNA recognition," *PNAS*, 93:12834–12839 (1996).

Jamieson et al., "In Vitro Selection of Zinc Fingers with Altered DNA–Binding Specificity," *Biochemistry*, 33(19):5689–5695 (1994).

Julian et al., "Replacement of His23 by Cys in a zinc finger of HIV–1 NCp7 led to a change in 1H NMR–derived 3D structure and to a loss of biological activity," *FEBS Letters*, 331(1,2):43–48 (1993).

Kamiuchi et al., "New multi zinc finger protein: biosynthetic design and characteristics of DNA recognition," *Nucleic Acids Symposium Series*, 37:153–154 (1997).

Kim et al., "Serine at Position 2 in the DNA Recognition helix of a Cys2–His2 Zinc finger Peptide is Not, in General, Responsible for Base Recognition," *J. Mol. Biol.*, 252:1–5 (1995).

Kim et al., "Site–specific cleavage of DNA–RNA hybrids by zinc finger/FokI cleavage domain fusions," *Gene*, 203:43–49 (1997).

Kim et al., "A 2.2 A° resolution crystal structure of a designed zinc finger protein bound to DNA," *Nat. Struct. Biol.*, 3(11):940–945 (1996).

Kim et al., "Getting a handhold on DNA: Design of poly–zinc finger proteins with femtomolar dissociation constants," *PNAS*, 95:2812–2817 (1998).

Kim et al., "Design of TATA box–binding protein/zinc finger fusions for targeted regulation of gene expression," *PNAS*, 94:3616–3620 (1997).

Kim et al., "Hybrid restriction enzymes: Zinc finger fusions to Fok I cleavage domain," *PNAS*, 93:1156–1160 (1996).

Kinzler et al., "The GLI gene is a member of the Kruppel family of zinc finger proteins," *Nature*, 332:371–4 (1988).

Klug, A., "Gene Regulatory Proteins and Their Interaction with DNA," *Ann. NY Acad. Sci.*, 758:143–160 (1995).

Klug et al., "Protein Motifs 5: Zinc Fingers," *FASEB J.*, 9:597–604 (1995).

Kulda et al., "The regulatory gene areA mediating nitrogen metabolite repression in *Aspergillus nidulans*. Mutations affecting specificty of gene activation alter a loop residue of a putative zinc finger," *EMBO J.*, 9(5):1355–1364 (1990).

Laird–Offringa et al., "RNA–binding proteins tamed," *Nat. Structural Biol.*, 5(8):665–668 (1998).

Mandel–Gutfreund et al., "Quantitative parameters for amino acid–base interaction: implications for prediction of protein–DNA binding sites," *Nuc. Acids Res.*, 26(10):2306–2312 (1998).

Mizushima et al., "pEF–BOS, a powerful mammilian expression vector," *Nuc. Acids Res.*, 18(17):5322 (1990).

Nardelli et al., "Zinc finger–DNA recognition: analysis of base specificity by site–directed mutagenesis," *Nuc. Acids Res.*, 20(16):4137–4144 (1992).

Nardelli et al., "Base sequence discrimination by zinc–finger DNA–binding domains," *Nature*, 349:175–178 (1991).

Nekludova et al., "Distinctive DNA conformation with enlarged major groove is found in Zn–finger—DNA and other protein—DNA complexes," *PNAS*, 91:6948–6952 (1994).

Orkin et al., "Report and Recommendations of the Panel to Asses the NIH Investment in Research on Gene Therapy" (1995).

Pabo et al., "Systematic Analysis of Possible Hydrogen Bonds between Amino Acid Side Chains and B-form DNA," *J. Biomolecular Struct. Dynamics*, 1:1039–1049 (1983).

Pabo et al., "Protein–DNA Recognition," *Ann. Rev. Biochem.*, 53:293–321 (1984).

Pabo, C. O., "Transcription Factors: Structural Families and Principals of DNA Recognition," *Ann. Rev. Biochem.*, 61:1053–1095 (1992).

Pavletich et al., "Crystal Structure of a Five-Finger GLI–DNA Complex: New Perspectives on Zinc Fingers," *Science*, 261:1701–1707 (1993).

Pavletich et al., "Zinc Finger–DNA Recognition: Crystal Structure of a Zif268–DNA Complex at 2.1 Å," *Science*, 252:809–817 (1991).

Pengue et al., "Repression of transcriptional activity at a distance by the evolutionarily conserved KRAB domain present in a subfamily of zinc finger proteins," *Nuc. Acids Res.*, 22(15):2908–2914 (1994).

Pengue et al., "Transcriptional Silencing of Human Immunodeficiency Virus Type 1 Long Terminal Repeat–Driven Gene Expression by the Kruppel–Associated Box Repressor Domain Targeted to the Transactivating Response Element," *J. Virology*, 69(10):6577–6580 (1995).

Pengue et al., "Kruppel–associated box–mediated repression of RNA polymerase II promoters is influenced by the arrangement of basal promoter elements," *PNAS*, 93:1015–1020 (1996).

Pomerantz et al., "Structure–Based Design of a Dimeric Zinc Finger Protein," *Biochemistry*, 37(4):965–970 (1998).

Qian et al., "Two–Dimensional NMR Studies of the Zinc Finger Motif: Solution Structures and Dynamics of Mutant ZFY Domains Containing Aromatic Substitutions in the Hydrophobic Core," *Biochemitsry*, 31:7463–7476 (1992).

Quigley et al., "Complete Androgen Insensitivity Due to Delection of Exon C of the Androgen Receptor Gene Highlights the Functional Importance of the Second Zinc Finger of the Androgen Receptor in Vivo," *Molecular Endocrinology*, 6(7):1103–1112 (1992).

Rauscher et al., "Binding of the Wilms' Tumor Locus Zinc Finger Protein to the EGR–1 Consensus Sequence," *Science*, 250:1259–1262 (1990).

Ray et al., "Repressor to activator switch by mutations in the first Zn finger of the glucocorticoid receptor: Is direct DNA binding necessary?, " *PNAS*, 88:7086–7090 (1991).

Rebar et al., "Phage Display Methods for Selecting Zinc Finger Proteins with Novel DNA–Binding Specificities," *Methods in Enzymology*, 267:129–149 (1996).

Rebar et al., "Zinc Finger Phage: Affinity Selection of Fingers with New DNA–Binding Specificities," *Science*, 263:671–673 (1994).

Reith et al., "Cloning of the major histocompatibility complex class II promoter binding protein affected in a hereditary defect in class II gene regulation," *PNAS*, 86:4200–4204 (1989).

Rice et al., "Inhibitors of HIV Nucleocapsid Protein Zinc Fingers as Candidates for the Treatment of AIDS," *Science*, 270:1194–1197 (1995).

Rivera et al., "A humanized system for pharmacologic control of gene expression," *Nature Medicine*, 2(9):1028–1032 (1996).

Rollins et al., "Role of TFIIIA Zinc Fingers In vivo: Analysis of Single–Finger Function in Developing Xenopus Embryos," *Molecular Cellular Biology*, 13(8):4776–4783 (1993).

Saleh et al., "A Novel Zinc Finger Gene on Human Chromosome 1qter That Is Alternatively Spliced in Human Tissues and Cell Lines," *Am. J. Hum. Genet.*, 52:192–203 (1993).

Shi et al., "Specific DNA–RNA Hybrid Binding by Zinc Finger Proteins," *Science*, 268:282–284 (1995).

Shi et al., "DNA Unwinding Induced by Zinc Finger Protein Binding," *Biochemistry*, 35:3845–3848 (1996).

Shi et al., "A direct comparison of the properties of natural and designed finger proteins," *Chem. & Biol.*, 2(2):83–89 (1995).

Singh et al., "Molecular Cloning of an Enhancer Binding Protein: Isolation by Screening of an Expression Library with a Recognition Site DNA," *Cell*, 52:415–423 (1988).

South et al., "The Nucleocapsid Protein Isolated from HIV–1 Particles Binds Zinc and Forms Retroviral–Type Zinc Fingers," *Biochemistry*, 29:7786–7789 (1990).

Suzuki et al., "Stereochemical basis of DNA recognition by Zn fingers," *Nuc. Acids Res.*, 22(16):3397–3405 (1994).

Suzuki et al. "DNA recognition code of transcription factors in the helix–turn–helix, probe helix, hormone receptor, and zinc finger families," *PNAS*, 91:12357–12361 (1994).

Swirnoff et al., "DNA–Binding Specificity of NGFI–A and Related Zinc Finger Transcription Factors," *Mol. Cell. Biol.*, 15(4):2275–2287 (1995).

Taylor et al, "Designing Zinc–Finer ADR1 Mutants with Altered Specificity of DNA Binding to T in UAS1 Sequences," *Biochemistry*, 34:3222–3230 (1995).

Thiesen et al., "Determination of DNA binding specificities of mutated zinc finger domains," *FEBS Letters*, 283(1):23–26 (1991).

Thiesen et al., "Amino Acid Substitutions in the SP1 Zinc Finger Domain Alter the DNA Binding Affinity to Cognate SP1 Target Site," *Biochem. Biophys. Res. Communications*, 175(1):333–338 (1991).

Thukral et al., "Localization of a Minimal Binding Domain and Activation Regions in Yeast Regulatory Protein ADR1," *Molecular Cellular Biology*, 9(6):2360–2369 (1989).

Thukral et al., "Two Monomers of Yeast Transcription Factor ADR1 Bind a Palindromic Sequence Symmetrically to Activate ADH2 Expression," *Molecular Cellular Biol.*, 11(3):1566–1577 (1991).

Thukral et al., "Alanine scanning site–directed mutagenesis of the zinc fingers of transcription factor ADR1: Residues that contact DNA and that transactivate," *PNAS*, 88:9188–9192 (1991), + correction page.

Thukral et al., "Mutations in the Zinc Fingers of ADR1 That Change the Specificity of DNA Binding and Transactivation," *Mol. Cell Biol.*, 12(6):2784–2792 (1992).

Vortkamp et al., "Identification of Optimized Target Sequences for the GL13 Zinc Finger Protein," *DNA Cell Biol.*, 14(7):629–634 (1995).

Webster et al., "Conversion of the E1A Cys4 zinc finger to a nonfunctional His2, Cys2 zinc finger by a single point mutation," *PNAS*, 88:9989–9993 (1991).

Whyatt et al., "Two zinc finger–like domains of GATA–1 have different DNA binding specificities," *EMBO J.*, 12(13):4993–5005 (1993).

Wilson, et al., "In Vivo Mutational analysis of the NGFI–A Zinc Fingers*," *J. Biol. Chem.*, 267(6):3718–3724 (92).

Witzgall et al., "The Kruppel–associated box–A (KRAB–A) domain of zinc finger proteins mediates transcriptional repression," *PNAS*, 91:4514–4518 (1994).

Wright et al., "Expression of a Zinc Finger Gene in HTLV–I– and HTLV–II–transformed Cells," *Science*, 248:588–591 (1990).

Wu et al., "Building zinc fingers by selection: Toward a therapeutic application," *PNAS*, 92:344–348 (1995).

Yang et al., "Surface plasmon resonance based kinetic studies of zinc finger–DNA interactions," *J. Immunol. Methods*, 183:175–182 (1995).

Yu et al., "A haripin ribozyme inhibits expression of diverse strains of human immunodeficiency virus type 1," *PNAS*, 90:6340–6344 (1993).

Berg, J.M., "Letting your fingers do the walking," *Nature Biotechnology*, 15:323 (1997).

Choo, Y. et al., "In vivo repression by a site–specific DNA–binding protein designed against an oncogenic sequence," *Nature*, 372:642–645 (1994).

Kim, J. and Carol O. Pabo, "Transcriptional Repression by Zinc Finger Peptides," *Journal of Biological Chemistry*, 272(47):29795–29800 (1997).

Liu, Q. et al., "Design of polydactyl zinc–finger proteins for unique addressing within complex genomes," *Proc. Natl. Acad. Sci. USA*, 94:5525–5530 (1997).

Pomerantz, J.L. et al., "Analysis of homeodomain function by structure–based design of a transcription factor," *Proc. Natl. Acad. Sci. USA*, 92:9752–9756 (1995).

Pomerantz, J.L. et al., "Structure–Based Design of Transcription Factors," *Science*, 267:93–96 (1995).

Rhodes, D. and Aaron Klug, "Zinc Fingers," *Scientific American*, pp. 56–65 (1993).

Wu et al, Human Immunodeficiency Virus Type 1 Nucleocapsid Protein Reduces Reverse Transcriptase Pausing at a Secondary Structure near the Murine Leukemia Virus Polypuring Tract, Oct. 1996, Journal of Virology, vol. 70, No. 10, pp. 7132–7142.*

Donze et al. Activation of delta–globin gene expression by erythroid Krupple–like factor: A potential approach for gene therapy o sickle cell disease. Blood, vol. 88, pp. 4051–4057 (1996).*

* cited by examiner

FUNCTIONAL GENOMICS USING ZINC FINGER PROTEINS

CROSS-REFERENCES TO RELATED APPLICATIONS

This application is related to U.S. application Ser. No. 09/229,007, filed Jan. 12, 1999, and U.S. application Ser. No. 09/229,037, filed Jan. 12, 1999, are both incorporated by reference in their entirety.

STATEMENT REGARDING FEDERALLY SPONSORED RESEARCH AND DEVELOPMENT

Not applicable.

FIELD OF THE INVENTION

The present invention provides methods of regulating gene expression using recombinant zinc finger proteins, for functional genomics and target validation applications.

BACKGROUND OF THE INVENTION

Determining the function of a gene of interest is important for identifying potential genomic targets for drug discovery. Genes associated with a particular function or phenotype can then be validated as targets for discovery of therapeutic compounds. Historically, the function of a particular gene has been identified by associating expression of the gene with a specification function of phenotype in a biological system such as a cell or a transgenic animal.

One known method used to validate the function of a gene is to genetically remove the gene from a cell or animal (i.e., create a "knockout") and determine whether or not a phenotype (i.e., any change, e.g., morphological, functional, etc., observable by an assay) of the cell or animal has changed. This determination depends on whether the cell or organism survives without the gene and is not feasible if the gene is required for survival. Other genes are subject to counteracting mechanisms that are able to adapt to the disappearance of the gene and compensate for its function in other ways. This compensation may be so effective, in fact, that the true function of the deleted gene may go unnoticed. The technical process of creating a "knockout" is laborious and requires extensive sequence information, thus commanding immense monetary and technical resources if undertaken on a genome wide scale.

In another example, antisense methods of gene regulation and methods that rely on targeted ribozymes are highly unpredictable. Another method for experimentally determining the function of a newly discovered gene is to clone its cDNA into an expression vector driven by a strong promoter and measure the physiological consequence of its over-expression in a transfected cell. This method is also labor intensive and does not address the physiological consequences of down-regulation of a target gene. Therefore, simple methods allowing the selective over- and under-expression of uncharacterized genes would be of great utility to the scientific community. Methods that permit the regulation of genes in cell model systems, transgenic animals and transgenic plants would find widespread use in academic laboratories, pharmaceutical companies, genomics companies and in the biotechnology industry.

An additional use of target validation is in the production of in vivo and in vitro assays for drug discovery. Once the gene causing a selected phenotype has been identified, cell lines, transgenic animals and transgenic plants could be engineered to express a useful protein product or repress a harmful one. These model systems are then used, e.g., with high throughput screening methodology, to identify lead therapeutic compounds that regulate expression of the gene of choice, thereby providing a desired phenotype, e.g., treatment of disease.

Methods currently exist in the art, which allow one to alter the expression of a given gene, e.g., using ribozymes, antisense technology, small molecule regulators, over-expression of cDNA clones, and gene-knockouts. As described above, these methods have to date proven to be generally insufficient for many applications and typically have not demonstrated either high target efficacy or high specificity in vivo. For useful experimental results and therapeutic treatments, these characteristics are desired.

Gene expression is normally controlled by sequence specific DNA binding proteins called transcription factors. These bind in the general proximity (although occasionally at great distances) of the point of transcription initiation of a gene and typically include both a DNA binding domain and a regulatory domain. They act to influence the efficiency of formation or function of a transcription initiation complex at the promoter. Transcription factors can act in a positive fashion (transactivation) or in a negative fashion (transrepression). Although transcription factors typically contain a regulatory domain, repression can also be achieved by steric hindrance via a DNA binding domain alone.

Transcription factor function can be constitutive (always "on") or conditional. Conditional function can be imparted on a transcription factor by a variety of means, but the majority of these regulatory mechanisms depend of the sequestering of the factor in the cytoplasm and the inducible release and subsequent nuclear translocation, DNA binding and transactivation (or repression). Examples of transcription factors that function this way include progesterone receptors, sterol response element binding proteins (SREBPs) and NF-kappa B. There are examples of transcription factors that respond to phosphorylation or small molecule ligands by altering their ability to bind their cognate DNA recognition sequence (Hou et al., *Science* 256:1701 (1994); Gossen & Bujard, *Proc. Natl. Acad. Sci. U.S.A.* 89:5547 (1992); Oligino et al., *Gene Ther.* 5:491–496 (1998); Wang et al., *Gene Ther.* 4:432–441(1997); Neering et al., *Blood* 88:1147–1155 (1996); and Rendahl et al., *Nat. Biotechnol.* 16:757–761 (1998)).

Zinc finger proteins ("ZFPs") are proteins that can bind to DNA in a sequence-specific manner. Zinc fingers were first identified in the transcription factor TFIIIA from the oocytes of the African clawed toad, *Xenopus laevis*. Zinc finger proteins are widespread in eukaryotic cells. An exemplary motif characterizing one class of these proteins ($Cys_2His_2$ class) is -Cys-$(X)_{2-4}$-Cys-$(X)_{12}$-His-$(X)_{3-5}$-His (SEQ ID NO: 1) (where X is any amino acid). A single finger domain is about 30 amino acids in length and several structural studies have demonstrated that it contains an alpha helix containing the two invariant histidine residues co-ordinated through zinc with the two cysteines of a single beta turn. To date, over 10,000 zinc finger sequences have been identified in several thousand known or putative transcription factors. Zinc finger proteins are involved not only in DNA-recognition, but also in RNA binding and protein-protein binding. Current estimates are that this class of molecules will constitute the products of about 2% of all human genes.

The X-ray crystal structure of Zif268, a three-finger domain from a murine transcription factor, has been solved in complex with its cognate DNA-sequence and shows that each finger can be superimposed on the next by a periodic rotation and translation of the finger along the main DNA axis. The structure suggests that each finger interacts independently with DNA over 3 base-pair intervals, with side-chains at positions -1, 2, 3 and 6 on each recognition helix making contacts with respective DNA triplet sub-site. The amino terminus of Zif268 is situated at the 3' end of its DNA recognition subsite. Recent results have indicated that some zinc fingers can bind to a fourth base in a target segment (Isalan et al., *Proc. Natl. Acad. Sci. U.S.A.* 94:5617–5621 (1997). The fourth base is on the opposite strand from the other three bases recognized by zinc finger and complementary to the base immediately 3' of the three base subsite.

The structure of the Zif268-DNA complex also suggested that the DNA sequence specificity of a zinc finger protein might be altered by making amino acid substitutions at the four helix positions (-1, 2, 3 and 6) on a zinc finger recognition helix. Phage display experiments using zinc finger combinatorial libraries to test this observation were published in a series of papers in 1994 (Rebar et al., *Science* 263:671–673 (1994); Jamieson et al., *Biochemistry* 33:5689–5695 (1994); Choo et al., *Proc. Natl. Acad. Sci. U.S.A.* 91:11163–11167 (1994)). Combinatorial libraries were constructed with randomized side-chains in either the first or middle finger of Zif268 and then isolated with an altered Zif268 binding site in which the appropriate DNA sub-site was replaced by an altered DNA triplet. Correlation between the nature of introduced mutations and the resulting alteration in binding specificity gave rise to a partial set of substitution rules for rational design of zinc finger proteins with altered binding specificity. Greisman & Pabo, *Science* 275:657–661 (1997) discuss an elaboration of a phage display method in which each finger of a zinc finger protein is successively subjected to randomization and selection. This paper reported selection of zinc finger proteins for a nuclear hormone response element, a p53 target site and a TATA box sequence.

Recombinant zinc finger proteins have been reported to have the ability to regulate gene expression of transiently expressed reporter genes in cultured cells (see, e.g., Pomerantz et al., *Science* 267:93–96 (1995); Liu et al., *Proc. Natl. Acad. Sci. U.S.A.* 94:5525–5530 1997); and Beerli et al., *Proc. Natl. Acad. Sci. U.S.A.* 95:14628–14633 (1998)). For example, Pomerantz et al., *Science* 267:93–96 (1995) report an attempt to design a novel DNA binding protein by fusing two fingers from Zif268 with a homeodomain from Oct-1. The hybrid protein was then fused with either a transcriptional activator or repressor domain for expression as a chimeric protein. The chimeric protein was reported to bind a target site representing a hybrid of the subsites of its two components. The authors then constructed a reporter vector containing a luciferase gene operably linked to a promoter and a hybrid site for the chimeric DNA binding protein in proximity to the promoter. The authors reported that their chimeric DNA binding protein could activate or repress expression of the luciferase gene.

Liu et al., *Proc. Natl. Acad. Sci. U.S.A.* 94:5525–5530 (1997) report forming a composite zinc finger protein by using a peptide spacer to link two component zinc finger proteins, each having three fingers. The composite protein was then further linked to transcriptional activation or repression domains. It was reported that the resulting chimeric protein bound to a target site formed from the target segments bound by the two component zinc finger proteins. It was further reported that the chimeric zinc finger protein could activate or repress transcription of a reporter gene when its target site was inserted into a reporter plasmid in proximity of a promoter operably linked to the reporter.

Beerli et al., *Proc. Natl. Acad. Sci. U.S.A.* 95:14628–14633 (1998) report construction of a chimeric six finger zinc finger protein fused to either a KRAB, ERD, or SID transcriptional repressor domain, or the VP16 or VP64 transcriptional activation domain. This chimeric zinc finger protein was designed to recognize an 18 bp target site in the 5' untranslated region of the human erbB-2 gene. Using this construct, the authors of this study report both activation and repression of a transiently expressed reporter luciferase construct linked to the erbB-2 promoter.

In addition, a recombinant zinc finger protein was reported to repress expression of an integrated plasmid construct encoding a bcr-abl oncogene (Choo et al., *Nature* 372:642–645 (1994)). The target segment to which the zinc finger proteins bound was a nine base sequence GCA GAA GCC chosen to overlap the junction created by a specific oncogenic translocation fusing the genes encoding bcr and abl. The intention was that a zinc finger protein specific to this target site would bind to the oncogene without binding to abl or bcr component genes. The authors used phage display to select a variant zinc finger protein that bound to this target segment. The variant zinc finger protein thus isolated was then reported to repress expression of a stably transfected bcr-abl construct in a cell line.

To date, these methods have focused on regulation of either transiently expressed, known genes, or on regulation of known exogenous genes that have been integrated into the genome. In contrast, specific regulation of a candidate gene or list of genes to identify the cause of a selected phenotype has not been demonstrated in the art. Therefore, a need exists for useful methods of identifying the biological function of a selected gene or genes and or validating a gene or genes as a suitable target for drug discovery.

SUMMARY OF THE INVENTION

The present invention thus provides for the first time methods of identifying a gene or genes associated a selected phenotype, e.g., for drug discovery, target validation, or functional genomics.

In one aspect, the present invention provides a method of identifying the biological function of a candidate gene, the method comprising the steps of: (i) selecting a first candidate gene; (ii) providing a first zinc finger protein that binds to a first target site of the first candidate gene and a second zinc finger protein that binds to a target site of a second gene; (iii) culturing a first cell under conditions where the first zinc finger protein contacts the first candidate gene and culturing a second cell under conditions where the second zinc finger protein contacts the second candidate gene, wherein the first and the second zinc finger proteins modulate expression of the first and second candidate genes; and (iv) assaying for a selected phenotype, thereby identifying whether or not the first candidate gene is associated with the selected phenotype.

In another aspect, the present invention provides a method of identifying the biological function of a candidate gene, the method comprising the steps of: (i) identifying a plurality of candidate genes; (ii) providing a first zinc finger protein that binds to a first target site of a first candidate gene; (iii) culturing a first cell under conditions where the first zinc finger protein contacts the first candidate gene, wherein the first zinc finger protein modulates expression of the first candidate gene; (iv) determining the expression pattern of the candidate genes and determining whether or not the first candidate gene is associated with the selected phenotype; and (v) repeating steps (ii)–(iv) for each candidate gene.

In another aspect, the present invention provides a method of identifying the biological function of a candidate gene, the method comprising the steps of: (i) selecting a first candidate gene; (ii) providing a first zinc finger that binds to a first target site of the first candidate gene and a second zinc finger that binds to a second target site of the first candidate gene; (iii) culturing a first cell under conditions where the first zinc finger protein contacts the first candidate gene, and culturing a second cell under conditions where the second zinc finger protein contacts the first candidate gene, wherein the first and the second zinc finger proteins modulate expression of the first candidate gene; and (iv) assaying for a selected phenotype, thereby identifying whether or not the first candidate gene is associated with the selected phenotype.

In another aspect, the present invention provides a method of identifying the biological function of a candidate gene, the method comprising the steps of: (i) selecting a first candidate gene; (ii) providing a first zinc finger protein that binds to a first target site of the first candidate gene; (iii) culturing a first cell under conditions where the first candidate zinc finger protein contacts the first candidate gene, wherein the first zinc finger proteins modulate expression of the first candidate gene; and (iv) assaying for a selected phenotype, thereby identifying whether or not the first candidate gene is associated with the selected phenotype.

In one embodiment, the method further comprises providing a third zinc finger protein that binds to a second target site of the first candidate gene. In one embodiment, the method further comprises provide a third zinc finger protein that binds to a target site of a second candidate gene. In another embodiment, the method further comprises selecting a plurality of candidate genes and providing a plurality of zinc finger proteins that bind to a target site of each candidate gene.

In one embodiment, the first candidate gene is partially encoded by an EST of at least about 200 nucleotides in length. In one embodiment, the first candidate gene and the second gene are both associated with the selected phenotype. In one embodiment, the second gene is a control gene. In one embodiment, the first and second cell are the same cell, wherein the cell comprises the first and second candidate genes. In one embodiment, the first and the second candidate genes are endogenous genes.

In one embodiment, expression of the candidate genes is inhibited by at least about 50%. In one embodiment, expression of the candidate genes is activated by at least about 150%. In one embodiment, the modulation of expression is activation of gene expression that prevents repression of gene expression. In one embodiment, the modulation of expression is inhibition of gene expression that prevents gene activation.

In one embodiment, the zinc finger proteins are fusion proteins comprising one or more regulatory domains. In one embodiment, the regulatory domain is selected from the group consisting of a transcriptional repressor, a methyl transferase, a transcriptional activator, a histone acetyltransferase, and a histone deacetylase.

In one embodiment, the cell is selected from the group consisting of animal cell, a plant cell, a bacterial cell, a protozoal cell, a fungal cell, a mammalian cell, or a human cell. In one embodiment, the cell comprises less than about $1.5 \times 10^6$ copies of each zinc finger protein.

In one embodiment, the first and second zinc finger proteins are encoded by an expression vector comprising a zinc finger protein nucleic acid operably linked to a promoter, and wherein the method further comprises the step of first administering the expression vector to the cell. In one embodiment, expression of the zinc finger proteins is induced by administration of an exogenous agent. In one embodiment, expression of the zinc finger proteins is under small molecule control. In one embodiment, expression of the first zinc finger protein and expression of the second zinc finger protein are under different small molecule control, wherein both the first and the second zinc finger protein are fusion proteins comprising a regulatory domain, and wherein the first and the second zinc finger proteins are expressed in the same cell. In one embodiment, both the first and second zinc finger proteins comprise regulatory domains that are repressors. In one embodiment, the first zinc finger protein comprises a regulatory domain that is an activator, and the second zinc finger protein comprises a regulatory domain that is a repressor.

In one embodiment, the expression vector is a viral vector. In another embodiment, the expression vector is a retroviral expression vector, an adenoviral expression vector, or an AAV expression vector. In one embodiment, the zinc finger proteins are encoded by a nucleic acid operably linked to an inducible promoter.

In one embodiment, the target site is upstream of a transcription initiation site of the candidate gene. In one embodiment, the target site is downstream of a transcription initiation site of the candidate gene. In one embodiment, the target site is adjacent to a transcription initiation site of the candidate gene. In another embodiment, the target site is adjacent to an RNA polymerase pause site downstream of a transcription initiation site of the candidate gene.

DETAILED DESCRIPTION OF THE INVENTION

Introduction

Figure 1:
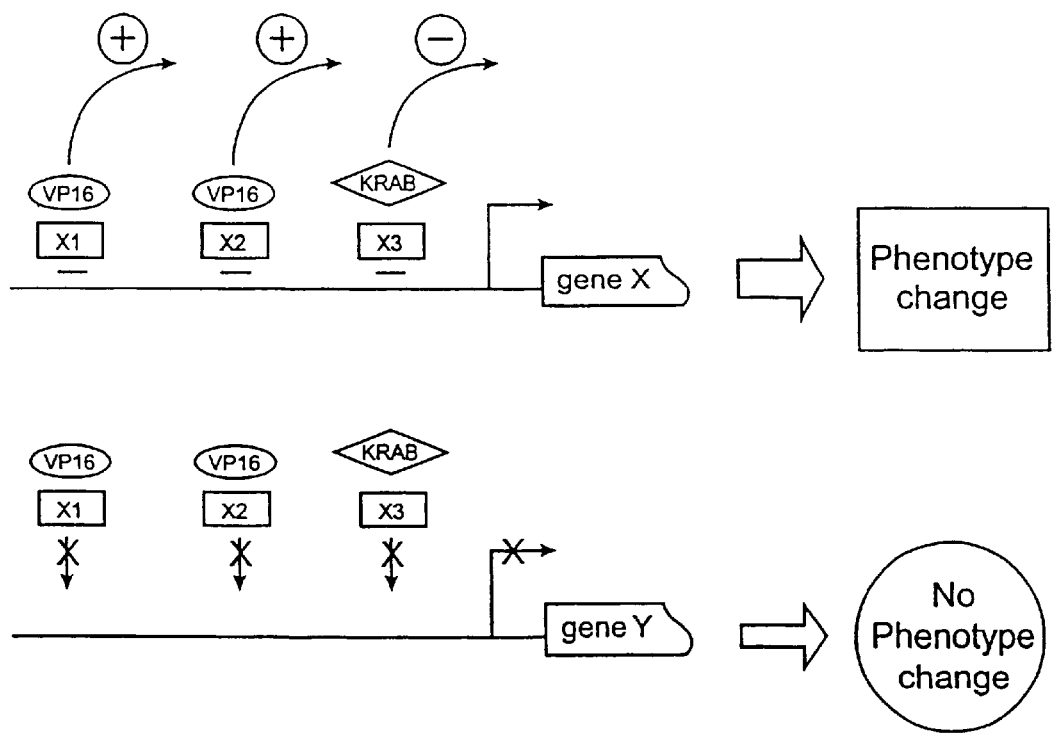
FIG. 1 shows schematic representation of target validation using zinc finger proteins to regulate gene expression.

As described herein, the present invention provides zinc finger proteins used in assays to determine the phenotypic consequences and function of gene expression. The recent advances in analytical techniques, coupled with focused mass sequencing efforts have created the opportunity to identify and characterize many more molecular targets than were previously available. This new information about genes and their functions will speed along basic biological understanding and present many new targets for therapeutic intervention. In some cases analytical tools have not kept pace with the generation of new data. An example is provided by recent advances in the measurement of global differential gene expression. These methods, typified by gene expression microarrays, differential cDNA cloning frequencies, subtractive hybridization and differential display methods, can very rapidly identify genes that are up or down-regulated in different tissues or in response to specific stimuli. Increasingly, such methods are being used to explore biological processes such as, transformation, tumor progression, the inflammatory response, neurological disorders etc. One can now very easily generate long lists of differentially expressed genes that correlate with a given physiological phenomenon, but demonstrating a causative relationship between a differentially expressed gene and the phenomenon is difficult. Until now, simple methods for assigning function to differentially expressed genes have not kept pace with the ability to monitor differential gene expression.

However, zinc finger protein technology can be used to rapidly analyze differential gene expression studies. Engineered zinc finger proteins can be readily used to up or down-regulate any candidate target gene. Very little sequence information is required to create a gene-specific DNA binding domain. This makes the zinc finger protein technology ideal for analysis of long lists of poorly characterized differentially expressed genes. One can simply build a zinc finger-based DNA binding domain for each candidate gene, create chimeric up and down-regulating artificial transcription factors and test the consequence of up or down-regulation on the phenotype under study (transformation, response to a cytokine etc.) by switching the candidate genes on or off one at a time in a model system.

Additionally, greater experimental control can be imparted by zinc finger proteins than can be achieved by more conventional methods. This is because the production and/or function of an engineered zinc finger protein can be placed under small molecule control. Examples of this approach are provided by the Tet-On system, the ecdysone-regulated system and a system incorporating a chimeric factor including a mutant progesterone receptor. These systems are all capable of indirectly imparting small molecule control on any candidate gene of interest or any transgene by placing the function and/or expression of a zinc finger protein regulator under small molecule control. In one embodiment, a cell comprises two zinc finger proteins. The zinc finger proteins either target two different candidate genes (i.e., two genes associated with the same phenotype), or two different target sites on the same candidate gene. Each zinc finger protein also comprises a regulatory domain. Expression of each zinc finger protein is under different small molecule control, allowing variations in the degree of activation or repression of gene expression.

The present application therefore provides for the first time methods of using zinc finger proteins for identifying a gene or genes associated a selected phenotype, e.g., for drug discovery target validation or for functional genomics. The present invention provides zinc finger DNA binding proteins that have been engineered to specifically recognize genes, with high efficacy. Modulation of gene expression using zinc finger proteins is used to determine the biological function of a gene, or a gene represented by an EST, and to validate the function of potential target genes for drug discovery.

In one embodiment, expression of at least two different genes is regulated, using different zinc finger proteins to regulate each gene. One of the genes is a candidate gene, and the other gene can be a control gene or a second candidate gene. Cells expressing the genes are contacted with zinc finger proteins, or nucleic acids encoding zinc finger proteins. Both the genes can be expressed in the same cell, or the genes can be each expressed in a different cell. After expression of the first and second genes is modulated by the zinc finger protein, the cells are assayed for changes in a selected phenotype, thereby identifying the function of the candidate gene or genes. In another embodiment, two zinc finger proteins target the same candidate gene at two different target sites. The methods of the invention can be applied both to functional genomics, which typically refers to identifying genes associated with a particular phenotype, and for target validation, which typically refers to identifying genes that are suitable for use in drug discovery assays.

As a result, the zinc finger proteins of the invention can be used to identify genes that cause a selected phenotype, both through activation and/or repression of gene transcription. Zinc finger proteins that bind to a promoter region can be used in the present invention, but zinc finger proteins can also regulate gene expression by binding to other regions of the gene. Extensive sequence information is therefore not required to examine expression of a candidate gene using zinc finger proteins. ESTs therefore can be used in the assays of the invention, to determine their biological function.

Furthermore, the zinc finger proteins can also be linked to regulatory domains, creating chimeric transcription factors to activate or repress transcription. In one embodiment, the methods of regulation use zinc finger proteins wherein the gene encoding the zinc finger protein is linked to molecular switches controlled by small molecules. The gene expression of the zinc finger proteins is therefore conditional and can be regulated using small molecules, thereby providing conditional regulation of candidate gene expression.

Such functional genomics assays allow for discovery of novel human and mammalian therapeutic applications, including the discovery of novel drugs, for, e.g., treatment of genetic diseases, cancer, fungal, protozoal, bacterial, and viral infection, ischemia, vascular disease, arthritis, immunological disorders, etc. Examples of assay systems for changes in phenotype include, e.g., transformation assays, e.g., changes in proliferation, anchorage dependence, growth factor dependence, foci formation, growth in soft agar, tumor proliferation in nude mice, and tumor vascularization in nude mice; apoptosis assays, e.g., DNA laddering and cell death, expression of genes involved in apoptosis; signal transduction assays, e.g., changes in intracellular calcium, cAMP, cGMP, IP3, changes in hormone and neurotransmittor release; receptor assays, e.g., estrogen receptor and cell growth; growth factor assays, e.g., EPO, hypoxia and erythrocyte colony forming units assays; enzyme product assays, e.g., FAD-2 induced oil desaturation; transcription assays, e.g., reporter gene assays; and protein production assays, e.g., VEGF ELISAs.

In one embodiment, a plurality of candidate genes is provided, and a first zinc finger protein is used to modulate expression of one of the candidate genes, while the expression pattern of the other candidate genes is examined. This step is repeated for each of the candidate genes, and changes in the expression patterns are used to determine the biological function of the genes. The expression data can then be analyzed to reconstruct the order or cascade of genes in a pathway that is associated with a selected phenotype.

As described herein, zinc finger proteins can be designed to recognize any suitable target site, for regulation of expression of any control or candidate gene of choice. Examples of target genes suitable for regulation include VEGF, CCR5, ERα, Her2/Neu, Tat, Rev, HBV C, S, X, and P, LDL-R, PEPCK, CYP7, Fibrinogen, ApoB, Apo E, Apo(a), renin, NF-κB, I-κB, TNF-α, FAS ligand, amyloid precursor protein, atrial naturetic factor, ob-leptin, ucp-1, IL-1, IL-2, IL-3, IL-4, IL-5, IL-6, IL-12, G-CSF, GM-CSF, Epo, PDGF, PAF, p53, Rb, fetal hemoglobin, dystrophin, eutrophin, GDNF, NGF, IGF-1, VEGF receptors flt and flk, topoisomerase, telomerase, bcl-2, cyclins, angiostatin, IGF, ICAM-1, STATS, c-myc, c-myb, TH, PTI-1, polygalacturonase, EPSP synthase, FAD2-1, delta-12 desaturase, delta-9 desaturase, delta-15 desaturase, acetyl-CoA carboxylase, acyl-ACP-thioesterase, ADP-glucose pyrophosphorylase, starch synthase, cellulose synthase, sucrose synthase, senescence-associated genes, heavy metal chelators, fatty acid hydroperoxide lyase, viral genes, protozoal genes, fungal genes, and bacterial genes. In general, suitable genes to be regulated include cytokines, lymphokines, growth factors, mitogenic factors, chemotactic factors, onco-active factors, receptors, potassium channels, G-proteins, signal transduction molecules, and other disease-related genes.

Candidate genes are selected by methods known to those of skill in the art, e.g., by gene expression microarrays, differential cDNA cloning frequencies, subtractive hybridization, differential display methods, by cloning ESTs from cells or tissues of interest, by identifying genes that are lethal upon knockout, by identifying genes that are up- or down-regulated in response to a particular developmental or cellular event or stimuli; by identifying genes that are up- or down-regulated in certain disease and pathogenic states, by identifying mutations and RFLPs, by identifying genes associated with regions of chromosomes known to be involved in inherited diseases, by identifying genes that are temporally regulated, e.g., in a pathogenic organism, differences based on SNPs, etc.

A general theme in transcription factor function is that simple binding and, in some cases, sufficient proximity to the promoter are all that is generally needed. Exact positioning relative to the promoter, orientation, and within limits, distance do not matter greatly. In some cases enhancers are found positioned large distances away from the gene of interest. In addition, for repression of gene expression, often simple steric hindrance of transcription initiation is sufficient. These features allow considerable flexibility in choosing target sites for zinc finger proteins. The target site recognized by the zinc finger protein therefore can be any suitable site in the target gene that will allow activation or repression of gene expression by a zinc finger protein, optionally linked to a regulatory domain. Preferred target sites include regions adjacent to, downstream, or upstream of the transcription start site. In addition, target sites that are located in enhancer regions, repressor sites, RNA polymerase pause sites, and specific regulatory sites (e.g., SP-1 sites, hypoxia response elements, nuclear receptor recognition elements, p53 binding sites), sites in the cDNA encoding region or in an expressed sequence tag (EST) coding region. As described below, typically each finger recognizes 2–4 base pairs, with a two finger zinc finger protein binding to a 4 to 7 bp target site, a three finger zinc finger protein binding to a 6 to 10 base pair site, and a six finger zinc finger protein binding to two adjacent target sites, each target site having from 6–10 base pairs.

Recognition of adjacent target sites by either associated or individual zinc finger proteins can be used to produce enhanced binding of the zinc finger proteins, resulting in an affinity that is greater than the affinity of the zinc finger proteins when individually bound to their target site. In one embodiment, a six finger zinc finger protein is produced as a fusion protein linked by an amino acid linker, and the resulting zinc finger protein recognizes an approximately 18 base pair target site (see, e.g., Liu et al., *Proc. Natl. Acad. Sci. U.S.A.* 94:5525–5530 (1997)). An 18 base pair target site is expected to provide specificity in the human genome, as a target site of that size should occur only once in every $3 \times 10^{10}$ base pairs, and the size of the human genome is $3.5 \times 10^9$ base pairs (see, e.g., Liu et al., *Proc. Natl. Acad. Sci. U.S.A.* 94:5525–5530 (1997)). In another embodiment, the two three-fingered portions of the six fingered zinc finger protein are non-covalently associated, through a leucine zipper, a STAT protein N-terminal domain, or the FK506 binding protein (see, e.g., O'Shea, *Science* 254: 539 (1991), Barahmand-Pour et al., *Curr. Top. Microbiol. Immunol.* 211:121–128 (1996); Klemm et al., *Annu. Rev. Immunol.* 16:569–592 (1998); Ho et al., *Nature* 382:822–826 (1996)).

As described herein, two zinc finger proteins are administered to a cell, recognizing different target genes, e.g., a candidate gene and a control gene, or two candidate genes, or two different target sites for the same gene. Optionally, a plurality of zinc finger proteins can be administered, which recognize two or more different target sites in the same gene. When two candidate genes are examined, both the first and the second gene may be required for the phenotype. The candidate genes may be endogenous genes or exogenous genes. In one embodiment, more than one candidate gene is associated with a selected phenotype.

In another embodiment, the zinc finger protein is linked to at least one or more regulatory domains, described below. Preferred regulatory domains include transcription factor repressor or activator domains such as KRAB and VP 16, co-repressor and co-activator domains, DNA methyl transferases, histone acetyltransferases, histone deacetylases, and endonucleases such as Fok1. For repression of gene expression, typically the expression of the gene is reduced by about 20% (i.e., 80% of non-zinc finger protein modulated expression), more preferably by about 50% (i.e., 50% of non-zinc finger protein modulated expression), more preferably by about 75–100% (i.e., 25% to 0% of non-zinc finger protein modulated expression). For activation of gene expression, typically expression is activated by about 1.5 fold (i.e., 150% of non-zinc finger protein modulated expression), preferably 2 fold (i.e., 200% of non-zinc finger protein modulated expression), more preferably 5–10 fold (i.e., 500–1000% of non-zinc finger protein modulated expression), up to at least 100 fold or more.

The expression of engineered zinc finger protein activators and repressors can be also controlled by small molecule systems typified by the tet-regulated systems and the RU-486 system (see, e.g., Gossen & Bujard, *Proc. Natl. Acad. Sci. U.S.A.* 89:5547 (1992); Oligino et al., *Gene Ther.* 5:491–496 (1998); Wang et al., *Gene Ther.* 4:432–441 (1997); Neering et al., *Blood* 88:1147–1155 (1996); and Rendahl et al., *Nat. Biotechnol.* 16:757–761 (1998)). These impart small molecule control on the expression of the zinc finger protein activators and repressors and thus impart small molecule control on the target gene(s) of interest. This beneficial feature could be used in cell culture models, and in transgenic animals and plants.

Definitions

As used herein, the following terms have the meanings ascribed to them unless specified otherwise.

A "candidate gene" refers to a cellular, viral, episomal, microbial, protozoal, fungal, animal, plant, chloroplastic, or mitochondrial gene. This term also refers to a microbial or viral gene that is part of a naturally occurring microbial or viral genome in a microbially or virally infected cell. The microbial or viral genome can be extrachromosomal or integrated into the host chromosome. This term also encompasses endogenous and exogenous genes, as well as cellular genes that are identified as ESTs. Often, the candidate genes of the invention are those for which the biological function is unknown. An assay of choice is used to determine whether or not the gene is associated with a selected phenotype upon regulation of candidate gene expression with a zinc finger protein. If the biological function is known, typically the candidate gene acts as a control gene, or is used to determine if one or more additional genes are associated with the same phenotype, or is used to determine if the gene participates with other genes in a particular phenotype.

A "selected phenotype" refers to any phenotype, e.g., any observable characteristic or functional effect that can be measured in an assay such as changes in cell growth, proliferation, morphology, enzyme function, signal transduction, expression patterns, downstream expression patterns, reporter gene activation, hormone release, growth factor release, neurotransmittor release, ligand binding, apoptosis, and product formation. Such assays include, e.g., transformation assays, e.g., changes in proliferation, anchorage dependence, growth factor dependence, foci formation, growth in soft agar, tumor proliferation in nude mice, and tumor vascularization in nude mice; apoptosis assays, e.g., DNA laddering and cell death, expression of genes involved in apoptosis; signal transduction assays, e.g., changes in intracellular calcium, cAMP, cGMP, IP3, changes in hormone and neurotransmittor release; receptor assays, e.g., estrogen receptor and cell growth; growth factor assays, e.g., EPO, hypoxia and erythrocyte colony forming units assays; enzyme product assays, e.g., FAD-2 induced oil desaturation; transcription assays, e.g., reporter gene assays; and protein production assays, e.g., VEGF ELISAs.

A candidate gene is "associated with" a selected phenotype if modulation of gene expression of the candidate gene causes a change in the selected phenotype.

The term "zinc finger protein" or "ZFP" refers to a protein having DNA binding domains that are stabilized by zinc. The individual DNA binding domains are typically referred to as "fingers" A zinc finger protein has least one finger, typically two fingers, three fingers, or six fingers. Each finger binds from two to four base pairs of DNA, typically three or four base pairs of DNA. A zinc finger protein binds to a nucleic acid sequence called a target site or target segment. Each finger typically comprises an approximately 30 amino acid, zinc-coordinating, DNA-binding subdomain. An exemplary motif characterizing one class of these proteins ($Cys_2His_2$ class) is -Cys-$(X)_{2-4}$-Cys-$(X)_{12}$-His-$(X)_{3-5}$-His (SEQ ID NO:1) (where X is any amino acid). Studies have demonstrated that a single zinc finger of this class consists of an alpha helix containing the two invariant histidine residues co-ordinated with zinc along with the two cysteine residues of a single beta turn (see, e.g., Berg & Shi, *Science* 271:1081–1085 (1996)).

A "target site" is the nucleic acid sequence recognized by a zinc finger protein. A single target site typically has about four to about ten base pairs. Typically, a two-fingered zinc finger protein recognizes a four to seven base pair target site, a three-fingered zinc finger protein recognizes a six to ten base pair target site, and a six fingered zinc finger protein recognizes two adjacent nine to ten base pair target sites.

The term "adjacent target sites" refers to non-overlapping target sites that are separated by zero to about 5 base pairs.

"$K_d$" refers to the dissociation constant for the compound, i.e., the concentration of a compound (e.g., a zinc finger protein) that gives half maximal binding of the compound to its target (i.e., half of the compound molecules are bound to the target) under given conditions (i.e., when [target] $<<K_d$), as measured using a given assay system (see, e.g., U.S. Pat. No. 5,789,538). The assay system used to measure the $K_d$ should be chosen so that it gives the most accurate measure of the actual $K_d$ of the zinc finger protein. Any assay system can be used, as long is it gives an accurate measurement of the actual $K_d$ of the zinc finger protein. In one embodiment, the $K_d$ for the zinc finger proteins of the invention is measured using an electrophoretic mobility shift assay ("EMSA"), as described herein. Unless an adjustment is made for zinc finger protein purity or activity, the $K_d$ calculations made using the methods described herein may result in an underestimate of the true $K_d$ of a given zinc finger protein. Optionally, the $K_d$ of a zinc finger protein used to modulate transcription of a candidate gene is less than about 100 nM, or less than about 75 nM, or less than about 50 nM, or less than about 25 nM.

The phrase "adjacent to a transcription initiation site" refers to a target site that is within about 50 bases either upstream or downstream of a transcription initiation site. "Upstream" of a transcription initiation site refers to a target site that is more than about 50 bases 5' of the transcription initiation site. "Downstream" of a transcription initiation site refers to a target site that is more than about 50 bases 3' of the transcription initiation site.

The phrase "RNA polymerase pause site" is described in Uptain et al., *Annu. Rev. Biochem.* 66:117–172 (1997).

"Administering" an expression vector, nucleic acid, zinc finger protein, or a delivery vehicle to a cell comprises transducing, transfecting, electroporating, tanslocating, fusing, phagocytosing, or biolistic methods, etc., i.e., any means by which a protein or nucleic acid can be transported across a cell membrane and preferably into the nucleus of a cell, including administration of naked DNA.

A "delivery vehicle" refers to a compound, e.g., a liposome, toxin, or a membrane translocation polypeptide, which is used to administer a zinc finger protein. Delivery vehicles can also be used to administer nucleic acids encoding zinc finger proteins, e.g., a lipid:nucleic acid complex, an expression vector, a virus, and the like.

The terms "modulating expression" "inhibiting expression" and "activating expression" of a gene refer to the ability of a zinc finger protein to activate or inhibit transcription of a gene. Activation includes prevention of transcriptional inhibition (i.e., prevention of repression of gene expression) and inhibition includes prevention of transcriptional activation (i.e., prevention of gene activation).

"Activation of gene expression that prevents repression of gene expression" refers to the ability of a zinc finger protein to block or prevent binding of a repressor molecule.

"Inhibition of gene expression that prevents gene activation" refers to the ability of a zinc finger protein to block or prevent binding of an activator molecule.

Modulation can be assayed by determining any parameter that is indirectly or directly affected by the expression of the target gene. Such parameters include, e.g., changes in RNA or protein levels, changes in protein activity, changes in product levels, changes in downstream gene expression, changes in reporter gene transcription (luciferase, CAT, β-galactosidase, β-glucuronidase, GFP (see, e.g., Mistili & Spector, *Nature Biotechnology* 15:961–964 (1997)); changes in signal transduction, phosphorylation and dephosphorylation, receptor-ligand interactions, second messenger concentrations (e.g., cGMP, cAMP, IP3, and $Ca^{2+}$), cell growth, and neovascularization, etc., as described herein. These assays can be in vitro, in vivo, and ex vivo. Such functional effects can be measured by any means known to those skilled in the art, e.g., measurement of RNA or protein levels, measurement of RNA stability, identification of downstream or reporter gene expression, e.g., via chemiluminescence, fluorescence, colorimetric reactions, antibody binding, inducible markers, ligand binding assays; changes in intracellular second messengers such as cGMP and inositol triphosphate (IP3); changes in intracellular calcium levels; cytokine release, and the like, as described herein.

To determine the level of gene expression modulation by a zinc finger protein, cells contacted with zinc finger proteins are compared to control cells, e.g., without the zinc finger protein or with a non-specific zinc finger protein, to examine the extent of inhibition or activation. Control samples are assigned a relative gene expression activity value of 100%. Modulation/inhibition of gene expression is achieved when the gene expression activity value relative to the control is about 80%, preferably 50% (i.e., 0.5× the activity of the control), more preferably 25%, more preferably 5–0%. Modulation/activation of gene expression is achieved when the gene expression activity value relative to the control is 110%, more preferably 150% (i.e., 1.5× the activity of the control), more preferably 200–500%, more preferably 1000–2000% or more.

A "transcriptional activator" and a "transcriptional repressor" refer to proteins or effector domains of proteins that have the ability to modulate transcription, as described above. Such proteins include, e.g., transcription factors and co-factors (e.g., KRAB, MAD, ERD, SID, nuclear factor kappa B subunit p65, early growth response factor 1, and nuclear hormone receptors, VP 16, VP64), endonucleases, integrases, recombinases, methyltransferases, histone acetyltransferases, histone deacetylases etc. Activators and repressors include co-activators and co-repressors (see, e.g., Utley et al., *Nature* 394:498–502 (1998)).

A "regulatory domain" refers to a protein or a protein domain that has transcriptional modulation activity when tethered to a DNA binding domain, i.e., a zinc finger protein. Typically, a regulatory domain is covalently or non-covalently linked to a zinc finger protein to effect transcription modulation. Alternatively, a zinc finger protein can act alone, without a regulatory domain, to effect transcription modulation.

The term "heterologous" is a relative term, which when used with reference to portions of a nucleic acid indicates that the nucleic acid comprises two or more subsequences that are not found in the same relationship to each other in nature. For instance, a nucleic acid that is recombinantly produced typically has two or more sequences from unrelated genes synthetically arranged to make a new functional nucleic acid, e.g., a promoter from one source and a coding region from another source. The two nucleic acids are thus heterologous to each other in this context. When added to a cell, the recombinant nucleic acids would also be heterologous to the endogenous genes of the cell. Thus, in a chromosome, a heterologous nucleic acid would include an non-native (non-naturally occurring) nucleic acid that has integrated into the chromosome, or a non-native (non-naturally occurring) extrachromosomal nucleic acid.

Similarly, a heterologous protein indicates that the protein comprises two or more subsequences that are not found in the same relationship to each other in nature (e.g., a "fusion protein," where the two subsequences are encoded by a single nucleic acid sequence). See, e.g., Ausubel, supra, for an introduction to recombinant techniques.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (naturally occurring) form of the cell or express a second copy of a native gene that is otherwise normally or abnormally expressed, under expressed or not expressed at all.

A "promoter" is defined as an array of nucleic acid control sequences that direct transcription. As used herein, a promoter typically includes necessary nucleic acid sequences near the start site of transcription, such as, in the case of certain RNA polymerase II type promoters, a TATA element, enhancer, CCAAT box, SP-1 site, etc. As used herein, a promoter also optionally includes distal enhancer or repressor elements, which can be located as much as several thousand base pairs from the start site of transcription. The promoters often have an element that is responsive to transactivation by a DNA-binding moiety such as a polypeptide, e.g., a nuclear receptor, Ga14, the lac repressor and the like.

A "constitutive" promoter is a promoter that is active under most environmental and developmental conditions. An "inducible" promoter is a promoter that is active under certain environmental or developmental conditions.

The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

An "expression vector" is a nucleic acid construct, generated recombinantly or synthetically, with a series of specified nucleic acid elements that permit transcription of a particular nucleic acid in a host cell, and optionally, integration or replication of the expression vector in a host cell. The expression vector can be part of a plasmid, virus, or nucleic acid fragment, of viral or non-viral origin. Typically, the expression vector includes an "expression cassette," which comprises a nucleic acid to be transcribed operably linked to a promoter. The term expression vector also encompasses naked DNA operably linked to a promoter.

By "host cell" is meant a cell that contains a zinc finger protein or an expression vector or nucleic acid encoding a zinc finger protein. The host cell typically supports the replication and/or expression of the expression vector. Host cells may be prokaryotic cells such as *E. coli*, or eukaryotic cells such as yeast, fungal, protozoal, higher plant, insect, or amphibian cells, or mammalian cells such as CHO, HeLa, 293, COS-1, and the like, e.g., cultured cells (in vitro), explants and primary cultures (in vitro and ex vivo), and cells in vivo.

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605–2608 (1985); Rossolini et al., *Mol. Cell. Probes* 8:91–98 (1994)). The term nucleic acid is used interchangeably with gene, cDNA, mRNA, oligonucleotide, and polynucleotide.

The terms "polypeptide," "peptide" and "protein" are used interchangeably herein to refer to a polymer of amino acid residues. The terms also apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. or instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M) (see, e.g., Creighton, Proteins (1984)).

Design of Zinc Finger Proteins

The zinc finger proteins of the invention are engineered to recognize a selected target site in the candidate gene of choice. Typically, a backbone from any suitable $Cys_2His_2$ zinc finger protein, such as SP-1, SP-1C, or ZIF268, is used as the scaffold for the engineered zinc finger protein (see, e.g., Jacobs, *EMBO J.* 11:4507 (1992); Desjarlais & Berg, *Proc. Natl. Acad. Sci. U.S.A.* 90:2256–2260 (1993)). A number of methods can then be used to design and select a zinc finger protein with high affinity for its target (e.g., preferably with a $K_d$ of less than about 25 nM). As described above, a zinc finger protein can be designed or selected to bind to any suitable target site in the target candidate gene, with high affinity. Co-pending patent application U.S. Ser. No. 09/229,007, filed Jan. 12, 1999 (herein incorporated by reference), comprehensively describes methods for design, construction, and expression of zinc finger proteins for selected target sites.

Any suitable method known in the art can be used to design and construct nucleic acids encoding zinc finger proteins, e.g., phage display, random mutagenesis, combinatorial libraries, computer/rational design, affinity selection, PCR, cloning from cDNA or genomic libraries, synthetic construction and the like. (see, e.g., U.S. Pat. No. 5,786,538; Wu et al., *Proc. Natl. Acad. Sci. U.S.A.* 92:344–348 (1995); Jamieson et al., *Biochemistry* 33:5689–5695 (1994); Rebar & Pabo, *Science* 263:671–673 (1994); Choo & Klug, *Proc. Natl. Acad. Sci. U.S.A.* 91:11163–11167 (1994); Choo & Klug, *Proc. Natl. Acad. Sci. U.S.A.* 91: 11168–11172 (1994); Desjarlais & Berg, *Proc. Natl. Acad. Sci. U.S.A.* 90:2256–2260 (1993); Desjarlais & Berg, *Proc. Natl. Acad. Sci. U.S.A.* 89:7345–7349 (1992); Pomerantz et al., *Science* 267:93–96 (1995); Pomerantz et al., *Proc. Natl. Acad. Sci. U.S.A.* 92:9752–9756 (1995); and Liu et al., *Proc. Natl. Acad. Sci. U.S.A.* 94:5525–5530 (1997); Greisman & Pabo, *Science* 275:657–661 (1997); Desjarlais & Berg, *Proc. Natl. Acad. Sci. U.S.A.* 91:11-99-11103 (1994)).

In a preferred embodiment, copending application U.S. Ser. No. 09/229,007, filed Jan. 12, 1999 provides methods that select a target gene, and identify a target site within the gene containing one to six (or more) D-able sites (see definition below). Using these methods, a zinc finger protein can then be synthesized that binds to the preselected site. These methods of target site selection are premised, in part, on the recognition that the presence of one or more D-able sites in a target segment confers the potential for higher binding affinity in a zinc finger protein selected or designed to bind to that site relative to zinc finger proteins that bind to target segments lacking D-able sites. Experimental evidence supporting this insight is provided in Examples 2–9 of copending application U.S. Ser. No. 09/229,007, filed Jan. 12, 1999.

A D-able site or subsite is a region of a target site that allows an appropriately designed single zinc finger to bind to four bases rather than three of the target site. Such a zinc finger binds to a triplet of bases on one strand of a double-stranded target segment (target strand) and a fourth base on the other strand (see FIG. 2 of copending application U.S. Ser. No. 09/229,007, filed Jan. 12, 1999. Binding of a single zinc finger to a four base target segment imposes constraints both on the sequence of the target strand and on the amino acid sequence of the zinc finger. The target site within the target strand should include the "D-able" site motif 5' NNGK 3', in which N and K are conventional IUPAC-IUB ambiguity codes. A zinc finger for binding to such a site should include an arginine residue at position −1 and an aspartic acid, (or less preferably a glutamic acid) at position +2. The arginine residues at position −1 interacts with the G residue in the D-able site. The aspartic acid (or glutamic acid) residue at position +2 of the zinc finger interacts with the opposite strand base complementary to the K base in the D-able site. It is the interaction between aspartic acid (symbol D) and the opposite strand base (fourth base) that confers the name D-able site. As is apparent from the D-able site formula, there are two subtypes of D-able sites: 5' NNGG 3' and 5' NNGT 3'. For the former site, the aspartic acid or glutamic acid at position +2 of a zinc finger interacts with a C in the opposite strand to the D-able site. In the latter site, the aspartic acid or glutamic acid at position +2 of a zinc finger interacts with an A in the opposite strand to the D-able site. In general, NNGG is preferred over NNGT.

In the design of a zinc finger protein with three fingers, a target site should be selected in which at least one finger of the protein, and optionally, two or all three fingers have the potential to bind a D-able site. Such can be achieved by selecting a target site from within a larger target gene having the formula 5'-NNx aNy bNzc-3', wherein each of the sets (x, a), (y, b) and (z, c) is either (N, N) or (G, K);

at least one of (x, a), (y, b) and (z, c) is (G, K). and

N and K are IUPAC-IUB ambiguity codes

In other words, at least one of the three sets (x, a), (y, b) and (z, c) is the set (G, K), meaning that the first position of the set is G and the second position is G or T. Those of the three sets (if any) which are not (G, K) are (N, N), meaning that the first position of the set can be occupied by any nucleotide and the second position of the set can be occupied by any nucleotide. As an example, the set (x, a) can be (G, K) and the sets (y, b) and (z, c) can both be (N, N).

In the formula 5'-NNx aNy bNzc-3', the triplets of NNx aNy and bNzc represent the triplets of bases on the target strand bound by the three fingers in a zinc finger protein. If only one of x, y and z is a G, and this G is followed by a K, the target site includes a single D-able subsite. For example, if only x is G, and a is K, the site reads 5'-NNG KNy bNzc-3' with the D-able subsite highlighted. If both x and y but not z are G, and a and b are K, then the target site has two overlapping D-able subsites as follows: 5'-NNG KNG KNz c-3' (SEQ ID NO:2), with one such site being represented in bold and the other in italics. If all three of x, y and z are G and a, b, and c are K, then the target segment includes three D-able subsites, as follows 5'NNG KNG <u>KNG K</u>3' (SEQ ID NO:3), the D-able subsites being represented by bold, italics and underline.

These methods thus work by selecting a target gene, and systematically searching within the possible subsequences of the gene for target sites conforming to the formula 5'-NNx aNy bNzc-3', as described above. In some such methods, every possible subsequence of 10 contiguous bases on either strand of a potential target gene is evaluated to determine whether it conforms to the above formula, and, if so, how many D-able sites are present. Typically, such a comparison is performed by computer, and a list of target sites conforming to the formula are output. Optionally, such target sites can be output in different subsets according to how many D-able sites are present.

In a variation, the methods of the invention identify first and second target segments, each independently conforming to the above formula. The two target segments in such methods are constrained to be adjacent or proximate (i.e., within about 0–5 bases) of each other in the target gene. The strategy underlying selection of proximate target segments is to allow the design of a zinc finger protein formed by linkage of two component zinc finger proteins specific for the first and second target segments respectively. These principles can be extended to select target sites to be bound by zinc finger proteins with any number of component fingers. For example, a suitable target site for a nine finger protein would have three component segments, each conforming to the above formula.

The target sites identified by the above methods can be subject to further evaluation by other criteria or can be used directly for design or selection (if needed) and production of a zinc finger protein specific for such a site. A further criteria for evaluating potential target sites is their proximity to particular regions within a gene. If a zinc finger protein is to be used to repress a cellular gene on its own (i.e., without linking the zinc finger protein to a repressing moiety), then the optimal location appears to be at, or within 50 bp upstream or downstream of the site of transcription initiation, to interfere with the formation of the transcription complex (Kim & Pabo, *J. Biol. Chem.* 272:29795–296800 (1997)) or compete for an essential enhancer binding protein. If, however, a zinc finger protein is fused to a functional domain such as the KRAB repressor domain or the VP16 activator domain, the location of the binding site is considerably more flexible and can be outside known regulatory regions. For example, a KRAB domain can repress transcription at a promoter up to at least 3 kbp from where KRAB is bound (Margolin et al., *Proc. Natl. Acad. Sci. U.S.A.* 91:4509–4513 (1994)). Thus, target sites can be selected that do not necessarily include or overlap segments of demonstrable biological significance with target genes, such as regulatory sequences. Other criteria for further evaluating target segments include the prior availability of zinc finger proteins binding to such segments or related segments, and/or ease of designing new zinc finger proteins to bind a given target segment.

After a target segment has been selected, a zinc finger protein that binds to the segment can be provided by a variety of approaches. The simplest of approaches is to provide a precharacterized zinc finger protein from an existing collection that is already known to bind to the target site. However, in many instances, such zinc finger proteins do not exist. An alternative approach can also be used to design new zinc finger proteins, which uses the information in a database of existing zinc finger proteins and their respective binding affinities. A further approach is to design a zinc finger protein based on substitution rules as discussed above. A still further alternative is to select a zinc finger protein with specificity for a given target by an empirical process such as phage display. In some such methods, each component finger of a zinc finger protein is designed or selected independently of other component fingers. For example, each finger can be obtained from a different preexisting zinc finger protein or each finger can be subject to separate randomization and selection.

Once a zinc finger protein has been selected, designed, or otherwise provided to a given target segment, the zinc finger protein or the DNA encoding it are synthesized. Exemplary methods for synthesizing and expressing DNA encoding zinc finger proteins are described below. The zinc finger protein or a polynucleotide encoding it can then be used for modulation of expression, or analysis of the target gene containing the target site to which the zinc finger protein binds.

Expression and Purification of Zinc Finger Proteins

Zinc finger protein polypeptides and nucleic acids can be made using routine techniques in the field of recombinant genetics. Basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994)). In addition, essentially any nucleic acid can be custom ordered from any of a variety of commercial sources. Similarly, peptides and antibodies can be custom ordered from any of a variety of commercial sources.

Two alternative methods are typically used to create the coding sequences required to express newly designed DNA-binding peptides. One protocol is a PCR-based assembly procedure that utilizes six overlapping oligonucleotides (see FIG. 1 of copending patent application U.S. Ser. No. 09/229, 037). Three oligonucleotides correspond to "universal" sequences that encode portions of the DNA-binding domain between the recognition helices. These oligonucleotides remain constant for all zinc finger constructs. The other three "specific" oligonucleotides are designed to encode the recognition helices. These oligonucleotides contain substitutions primarily at positions −1, 2, 3 and 6 on the recognition helices making them specific for each of the different DNA-binding domains.

The PCR synthesis is carried out in two steps. First, a double stranded DNA template is created by combining the six oligonucleotides (three universal, three specific) in a four cycle PCR reaction with a low temperature annealing step, thereby annealing the oligonucleotides to form a DNA "scaffold." The gaps in the scaffold are filled in by high-fidelity thermostable polymerase, the combination of Taq and Pfu polymerases also suffices. In the second phase of construction, the zinc finger template is amplified by external primers designed to incorporate restriction sites at either end for cloning into a shuttle vector or directly into an expression vector.

An alternative method of cloning the newly designed DNA-binding proteins relies on annealing complementary oligonucleotides encoding the specific regions of the desired zinc finger protein. This particular application requires that the oligonucleotides be phosphorylated prior to the final ligation step. This is usually performed before setting up the annealing reactions, but kinasing can also occur post-annealing. In brief, the "universal" oligonucleotides encoding the constant regions of the proteins are annealed with their complementary oligonucleotides. Additionally, the "specific" oligonucleotides encoding the finger recognition helices are annealed with their respective complementary oligonucleotides. These complementary oligos are designed to fill in the region which was previously filled in by polymerase in the protocol described above. The complementary oligos to the common oligos 1 and finger 3 are engineered to leave overhanging sequences specific for the restriction sites used in cloning into the vector of choice. The second assembly protocol differs from the initial protocol in the following aspects: the "scaffold" encoding the newly designed zinc finger protein is composed entirely of synthetic DNA thereby eliminating the polymerase fill-in step, additionally the fragment to be cloned into the vector does not require amplification. Lastly, the design of leaving sequence-specific overhangs eliminates the need for restriction enzyme digests of the inserting fragment.

The resulting fragment encoding the newly designed zinc finger protein is ligated into an expression vector. Expression vectors that are commonly utilized include, but are not limited to, a modified pMAL-c2 bacterial expression vector (New England BioLabs, "NEB") or a eukaryotic expression vector, pcDNA (Promega).

Any suitable method of protein purification known to those of skill in the art can be used to purify zinc finger proteins of the invention (see Ausubel, supra, Sambrook, supra). In addition, any suitable host can be used, e.g., bacterial cells, insect cells, yeast cells, mammalian cells, and the like.

In one embodiment, expression of the zinc finger protein fused to a maltose binding protein (MBP-ZFP) in bacterial strain JM109 allows for straightforward purification through an amylose column (NEB). High expression levels of the zinc finger chimeric protein can be obtained by induction with IPTG since the MBP-ZFP fusion in the pMal-c2 expression plasmid is under the control of the IPTG inducible tac promoter (NEB). Bacteria containing the MBP-ZFP fusion plasmids are inoculated in to 2×YT medium containing 10 $\mu$M ZnCl$_2$, 0.02% glucose, plus 50 $\mu$g/ml ampicillin and shaken at 37° C. At mid-exponential growth IPTG is added to 0.3 mM and the cultures are allowed to shake. After 3 hours the bacteria are harvested by centrifugation, disrupted by sonication, and then insoluble material is removed by centrifugation. The MBP-ZFP proteins are captured on an amylose-bound resin, washed extensively with buffer containing 20 mM Tris-HCl (pH 7.5), 200 mM NaCl, 5 mM DTT and 50 $\mu$M ZnCl$_2$, then eluted with maltose in essentially the same buffer (purification is based on a standard protocol from NEB). Purified proteins are quantitated and stored for biochemical analysis.

The biochemical properties of the purified proteins, e.g., $K_d$, can be characterized by any suitable assay. In one embodiment, $K_d$ is characterized via electrophoretic mobility shift assays ("EMSA") (Buratowski & Chodosh, in *Current Protocols in Molecular Biology* pp. 12.2.1–12.2.7 (Ausubel ed., 1996); see also U.S. Pat. No. 5,789,538, U.S. Ser. No. 09/229,007, filed Jan. 12, 1999, herein incorporated by reference). Affinity is measured by titrating purified protein against a low fixed amount of labeled double-stranded oligonucleotide target. The target comprises the natural binding site sequence (9 or 18 bp) flanked by the 3 bp found in the natural sequence. External to the binding site plus flanking sequence is a constant sequence. The annealed oligonucleotide targets possess a 1 bp 5' overhang which allows for efficient labeling of the target with T4 phage polynucleotide kinase. For the assay the target is added at a concentration of 40 nM or lower (the actual concentration is kept at least 10-fold lower than the lowest protein dilution) and the reaction is allowed to equilibrate for at least 45 min. In addition the reaction mixture also contains 10 mM Tris (pH 7.5), 100 mM KCl, 1 mM MgCl$_2$, 0.1 mM ZnCl$_2$, 5 mM DTT, 10% glycerol, 0.02% BSA (poly (dIdC) or (dAdT) (Pharmacia) can also added at 10–100 $\mu$g/$\mu$l).

The equilibrated reactions are loaded onto a 10% polyacrylamide gel, which has been pre-run for 45 min in Tris/glycine buffer. Bound and unbound labeled target is resolved with electrophoresis at 150 V (alternatively, 10–20% gradient Tris-HCl gels, containing a 4% polyacrylamide stacker, can be used). The dried gels are visualized by autoradiography or phosphoroimaging and the apparent $K_d$ is determined by calculating the protein concentration that gives half-maximal binding.

Similar assays can also include determining active fractions in the protein preparations. Active fractions are determined by stoichiometric gel shifts where proteins are titrated against a high concentration of target DNA. Titrations are done at 100, 50, and 25% of target (usually at micromolar levels).

In another embodiment, phage display libraries can be used to select zinc finger proteins with high affinity to the selected target site. This method differs fundamentally from direct design in that it involves the generation of diverse libraries of mutagenized zinc finger proteins, followed by the isolation of proteins with desired DNA-binding properties using affinity selection methods. To use this method, the experimenter typically proceeds as follows.

First, a gene for a zinc finger protein is mutagenized to introduce diversity into regions important for binding specificity and/or affinity. In a typical application, this is accomplished via randomization of a single finger at positions −1, +2, +3, and +6, and perhaps accessory positions such as +1, +2, +8, or +10.

Next, the mutagenized gene is cloned into a phage or phagemid vector as a fusion with, e.g., gene III of filamentous phage, which encodes the coat protein pIII. The zinc finger gene is inserted between segments of gene III encoding the membrane export signal peptide and the remainder of pIII, so that the zinc finger protein is expressed as an amino-terminal fusion with pIII in the mature, processed protein. When using phagemid vectors, the mutagenized zinc finger gene may also be fused to a truncated version of gene III encoding, minimally, the C-terminal region required for assembly of pIII into the phage particle.

The resultant vector library is transformed into E. coli and used to produce filamentous phage which express variant zinc finger proteins on their surface as fusions with the coat protein pIII (if a phagemid vector is used, then the this step requires superinfection with helper phage). The phage library is then incubated with target DNA site, and affinity selection methods are used to isolate phage which bind target with high affinity from bulk phage. Typically, the DNA target is immobilized on a solid support, which is then washed under conditions sufficient to remove all but the tightest binding phage. After washing, any phage remaining on the support are recovered via elution under conditions which totally disrupt zinc finger-DNA binding.

Recovered phage are used to infect fresh E. coli, which is then amplified and used to produce a new batch of phage particles. The binding and recovery steps are then repeated as many times as is necessary to sufficiently enrich the phage pool for tight binders such that these may be identified using sequencing and/or screening methods.

Regulatory Domains

The zinc finger proteins of the invention can optionally be associated with regulatory domains for modulation of gene expression. The zinc finger protein can be covalently or non-covalently associated with one or more regulatory domains, alternatively two or more regulatory domains, with the two or more domains being two copies of the same domain, or two different domains. The regulatory domains can be covalently linked to the zinc finger protein, e.g., via an amino acid linker, as part of a fusion protein. The zinc finger proteins can also be associated with a regulatory domain via a non-covalent dimerization domain, e.g., a leucine zipper, a STAT protein N terminal domain, or an FK506 binding protein (see, e.g., O'Shea, Science 254: 539 (1991), Barahmand-Pour et al., Curr. Top. Microbiol. Immunol. 211:121–128 (1996); Klemm et al., Annu. Rev. Immunol. 16:569–592 (1998); Klemm et al., Annu. Rev. Immunol. 16:569–592 (1998); Ho et al., Nature 382:822–826 (1996); and Pomeranz et al., Biochem. 37:965 (1998)). The regulatory domain can be associated with the zinc finger protein at any suitable position, including the C- or N-terminus of the zinc finger protein.

Common regulatory domains for addition to the zinc finger protein include, e.g., effector domains from transcription factors (activators, repressors, co-activators, co-repressors), silencers, nuclear hormone receptors, oncogene transcription factors (e.g., myc, jun, fos, myb, max, mad, rel, ets, bcl, myb, mos family members etc.); DNA repair enzymes and their associated factors and modifiers; DNA rearrangement enzymes and their associated factors and modifiers; chromatin associated proteins and their modifiers (e.g., kinases, acetylases and deacetylases); and DNA modifying enzymes (e.g., methyltransferases, topoisomerases, helicases, ligases, kinases, phosphatases, polymerases, endonucleases) and their associated factors and modifiers.

Transcription factor polypeptides from which one can obtain a regulatory domain include those that are involved in regulated and basal transcription. Such polypeptides include transcription factors, their effector domains, coactivators, silencers, nuclear hormone receptors (see, e.g., Goodrich et al., Cell 84:825–30 (1996) for a review of proteins and nucleic acid elements involved in transcription; transcription factors in general are reviewed in Barnes & Adcock, Clin. Exp. Allergy 25 Suppl. 2:46–9 (1995) and Roeder, Methods Enzymol. 273:165–71 (1996)). Databases dedicated to transcription factors are known (see, e.g., Science 269:630 (1995)). Nuclear hormone receptor transcription factors are described in, for example, Rosen et al., J. Med. Chem. 38:4855–74 (1995). The C/EBP family of transcription factors are reviewed in Wedel et al., Immunobiology 193:171–85 (1995). Coactivators and co-repressors that mediate transcription regulation by nuclear hormone receptors are reviewed in, for example, Meier, Eur. J. Endocrinol. 134(2):158–9 (1996); Kaiser et al., Trends Biochem. Sci. 21:342–5 (1996); and Utley et al., Nature 394:498–502 (1998)). GATA transcription factors, which are involved in regulation of hematopoiesis, are described in, for example, Simon, Nat. Genet. 11:9–11 (1995); Weiss et al., Exp. Hematol. 23:99–107. TATA box binding protein (TBP) and its associated TAF polypeptides (which include TAF30, TAF55, TAF80, TAF110, TAF150, and TAF250) are described in Goodrich & Tjian, Curr. Opin. Cell Biol. 6:403–9 (1994) and Hurley, Curr. Opin. Struct. Biol. 6:69–75 (1996). The STAT family of transcription factors are reviewed in, for example, Barahmand-Pour et al., Curr. Top. Microbiol. Immunol. 211:121–8 (1996). Transcription factors involved in disease are reviewed in Aso et al., J. Clin. Invest. 97:1561–9 (1996).

In one embodiment, the KRAB repression domain from the human KOX-1 protein is used as a transcriptional repressor (Thiesen et al., New Biologist 2:363–374 (1990); Margolin et al., Proc. Natl. Acad. Sci. U.S.A. 91:4509–4513 (1994); Pengue et al., Nucl. Acids Res. 22:2908–2914 (1994); Witzgall et al., Proc. Natl. Acad. Sci. U.S.A. 91:4514–4518 (1994)). In another embodiment, KAP-1, a KRAB co-repressor, is used with KRAB (Friedman et al., Genes Dev. 10:2067–2078 (1996)). Alternatively, KAP-1 can be used alone with a zinc finger protein. Other preferred transcription factors and transcription factor domains that act as transcriptional repressors include MAD (see, e.g., Sommer et al., *J. Biol. Chem.* 273:6632–6642 (1998); Gupta et al., *Oncogene* 16:1149–1159 (1998); Queva et al., *Oncogene* 16:967–977 (1998); Larsson et al., *Oncogene* 15:737–748 (1997); Laherty et al., *Cell* 89:349–356 (1997); and Cultraro et al., *Mol Cell. Biol.* 17:2353–2359 (19977)); FKHR (forkhead in rhapdosarcoma gene; Ginsberg et al., *Cancer Res.* 15:3542–3546 (1998); Epstein et al., *Mol. Cell. Biol.* 18:4118–4130 (1998)); EGR-1 (early growth response gene product-1; Yan et al., *Proc. Natl. Acad. Sci. U.S.A.* 95:8298–8303 (1998); and Liu et al., *Cancer Gene Ther.* 5:3–28 (1998)); the ets2 repressor factor repressor domain (ERD; Sgouras et al., *EMBO J.* 14:4781–4793 (1995)); and the MAD smSIN3 interaction domain (SID; Ayer et al., *Mol. Cell. Biol.* 16:5772–5781 (1996)).

In one embodiment, the HSV VP16 activation domain is used as a transcriptional activator (see, e.g., Hagmann et al., *J. Virol.* 71:5952–5962 (1997)). Other preferred transcription factors that could supply activation domains include the VP64 activation domain (Seipel et al., *EMBO J.* 11:4961–4968 (1996)); nuclear hormone receptors (see, e.g., Torchia et al., *Curr. Opin. Cell. Biol.* 10:373–383 (1998)); the p65 subunit of nuclear factor kappa B (Bitko & Barik, *J. Virol.* 72:5610–5618 (1998) and Doyle & Hunt, *Neuroreport* 8:2937–2942 (1997)); and EGR-1 (early growth response gene product-1; Yan et al., *Proc. Natl. Acad. Sci. U.S.A.* 95:8298–8303 (1998); and Liu et al., *Cancer Gene Ther.* 5:3–28 (1998)).

Kinases, phosphatases, and other proteins that modify polypeptides involved in gene regulation are also useful as regulatory domains for zinc finger proteins. Such modifiers are often involved in switching on or off transcription mediated by, for example, hormones. Kinases involved in transcription regulation are reviewed in Davis, *Mol. Reprod. Dev.* 42:459–67 (1995), Jackson et al., *Adv. Second Messenger Phosphoprotein Res.* 28:279–86 (1993), and Boulikas, *Crit. Rev. Eukaryot. Gene Expr.* 5:1–77 (1995), while phosphatases are reviewed in, for example, Schonthal & Semin, *Cancer Biol.* 6:239–48 (1995). Nuclear tyrosine kinases are described in Wang, *Trends Biochem. Sci.* 19:373–6 (1994).

As described, useful domains can also be obtained from the gene products of oncogenes (e.g., myc, jun, fos, myb, max, mad, rel, ets, bcl, myb, mos family members) and their associated factors and modifiers. Oncogenes are described in, for example, Cooper, *Oncogenes, The Jones and Bartlett Series in Biology* ($2^{nd}$ ed., 1995). The ets transcription factors are reviewed in Waslylk et al., *Eur. J. Biochem.* 211:7–18 (1993) and Crepieux et al., *Crit. Rev. Oncog.* 5:615–38 (1994). Myc oncogenes are reviewed in, for example, Ryan et al., *Biochem. J.* 314:713–21 (1996). The jun and fos transcription factors are described in, for example, *The Fos and Jun Families of Transcription Factors* (Angel & Herrlich, eds. 1994). The max oncogene is reviewed in Hurlin et al., *Cold Spring Harb. Symp. Quant. Biol.* 59:109–16. The myb gene family is reviewed in Kanei-Ishii et al., *Curr. Top. Microbiol. Immunol.* 211:89–98 (1996). The mos family is reviewed in Yew et al., *Curr. Opin. Genet. Dev.* 3:19–25 (1993).

Zinc finger proteins can include regulatory domains obtained from DNA repair enzymes and their associated factors and modifiers. DNA repair systems are reviewed in, for example, Vos, *Curr. Opin. Cell Biol.* 4:385–95 (1992); Sancar, *Ann. Rev. Genet.* 29:69–105 (1995); Lehmann, *Genet. Eng.* 17:1–19 (1995); and Wood, *Ann. Rev. Biochem.* 65:135–67 (1996). DNA rearrangement enzymes and their associated factors and modifiers can also be used as regulatory domains (see, e.g., Gangloff et al., *Experientia* 50:261–9 (1994); Sadowski, *FASEB J.* 7:760–7 (1993)).

Similarly, regulatory domains can be derived from DNA modifying enzymes (e.g., DNA methyltransferases, topoisomerases, helicases, ligases, kinases, phosphatases, polymerases) and their associated factors and modifiers. Helicases are reviewed in Matson et al., *Bioessays,* 16:13–22 (1994), and methyltransferases are described in Cheng, *Curr. Opin. Struct. Biol.* 5:4–10 (1995). Chromatin associated proteins and their modifiers (e.g., kinases, acetylases and deacetylases), such as histone deacetylase (Wolffe, *Science* 272:371–2 (1996)) are also useful as domains for addition to the zinc finger protein of choice. In one preferred embodiment, the regulatory domain is a DNA methyl transferase that acts as a transcriptional repressor (see, e.g., Van den Wyngaert et al., *FEBS Lett.* 426:283–289 (1998); Flynn et al., *J. Mol. Biol.* 279:101–116 (1998); Okano et al., *Nucleic Acids Res.* 26:2536–2540 (1998); and Zardo & Caiafa, *J. Biol. Chem.* 273:16517–16520 (1998)). In another preferred embodiment, endonucleases such as Fok1 are used as transcriptional repressors, which act via gene cleavage (see, e.g., WO95/09233; and PCT/US94/01201).

Factors that control chromatin and DNA structure, movement and localization and their associated factors and modifiers; factors derived from microbes (e.g., prokaryotes, eukaryotes and virus) and factors that associate with or modify them can also be used to obtain chimeric proteins. In one embodiment, recombinases and integrases are used as regulatory domains. In one embodiment, histone acetyltransferase is used as a transcriptional activator (see, e.g., Jin & Scotto, *Mol. Cell. Biol.* 18:4377–4384 (1998); Wolffe, *Science* 272:371–372 (1996); Taunton et al., *Science* 272:408–411 (1996); and Hassig et al., *Proc. Natl. Acad. Sci. U.S.A.* 95:3519–3524 (1998)). In another embodiment, histone deacetylase is used as a transcriptional repressor (see, e.g., Jin & Scotto, *Mol. Cell. Biol.* 18:4377–4384 (1998); Syntichaki & Thireos, *J. Biol. Chem.* 273:24414–24419 (1998); Sakaguchi et al., *Genes Dev.* 12:2831–2841 (1998); and Martinez et al., *J. Biol. Chem.* 273:23781–23785 (1998)).

Linker domains between polypeptide domains, e.g., between two zinc finger proteins or between a zinc finger protein and a regulatory domain, can be included. such linkers are typically polypeptide sequences, such as poly gly sequences of between about 5 and 200 amino acids. Preferred linkers are typically flexible amino acid subsequences which are synthesized as part of a recombinant fusion protein. For example, in one embodiment, the linker DGGGS (SEQ ID NO:4) is used to link two zinc finger proteins. In another embodiment, the flexible linker linking two zinc finger proteins is an amino acid subsequence comprising the sequence TGEKP (SEQ ID NO:5) (see, e.g., Liu et al., *Proc. Natl. Acad. Sci. U.S.A.* 5525–5530 (1997)). In another embodiment, the linker LRQKDGERP (SEQ ID NO:6) is used to link two zinc finger proteins. In another embodiment, the following linkers are used to link two zinc finger proteins: GGRR (SEQ ID NO:7) (Pomerantz et al. 1995, supra), $(G_4S)_n$ (SEQ ID NO:8) (Kim et al., *Proc. Natl. Acad. Sci. U.S.A.* 93, 1156–1160 (1996.); and GGRRGGS (SEQ ID NO:9); LRQRDGERP (SEQ ID NO:10); LRQKDGGGSERP (SEQ ID NO:11); LRQKD$(G_3S)_2$ERP (SEQ ID NO:12). Alternatively, flexible linkers can be rationally designed using computer program capable of modeling both DNA-binding sites and the peptides themselves (Desjarlais & Berg, *Proc. Natl. Acad. Sci. U.S.A.* 90:2256–2260 (1993), *Proc. Natl. Acad. Sci. U.S.A.* 91:11099–11103 (1994) or by phage display methods.

In other embodiments, a chemical linker is used to connect synthetically or recombinantly produced domain sequences. Such flexible linkers are known to persons of skill in the art. For example, poly(ethylene glycol) linkers are available from Shearwater Polymers, Inc. Huntsville, Ala. These linkers optionally have amide linkages, sulfhydryl linkages, or heterofunctional linkages. In addition to covalent linkage of zinc finger proteins to regulatory domains, non-covalent methods can be used to produce molecules with zinc finger proteins associated with regulatory domains.

In addition to regulatory domains, often the zinc finger protein is expressed as a fusion protein such as maltose binding protein ("MBP"), glutathione S transferase (GST), hexahistidine, c-myc, and the FLAG epitope, for ease of purification, monitoring expression, or monitoring cellular and subcellular localization.

Subcloning and Expression of Nucleic Acids Encoding Zinc Finger Protein

The nucleic acid encoding the zinc finger protein of choice is typically cloned into vectors for transformation into prokaryotic or eukaryotic cells for replication, expression, e.g., for determination of $K_d$. Such vectors are typically prokaryote vectors, e.g., plasmids, or shuttle vectors, or eukaryotic vectors such insect vectors, for storage or manipulation of the nucleic acid encoding zinc finger protein or production of protein, or eukaryotic vector such as viral vectors (e.g., adenoviral vectors, retroviral vector, etc.) for expression of zinc finger proteins and optionally regulation of gene expression. The nucleic acid encoding a zinc finger protein can then be administered to a plant cell, animal cell, a mammalian cell or a human cell, a fungal cell, a bacterial cell, or a protozoal cell.

To obtain expression of a cloned gene or nucleic acid, a zinc finger protein is typically subcloned into an expression vector that contains a promoter to direct transcription. Suitable bacterial and eukaryotic promoters are well known in the art and described, e.g., in Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994). Bacterial expression systems for expressing the zinc finger protein are available in, e.g., *E. coli*, Bacillus sp., and Salmonella (Palva et al., *Gene* 22:229–235 (1983)). Kits for such expression systems are commercially available. Eukaryotic expression systems for mammalian cells, yeast, and insect cells are well known in the art and are also commercially available.

The promoter used to direct expression of a zinc finger protein nucleic acid a depends on the particular application. For example, a strong constitutive promoter is typically used for expression and purification of zinc finger protein. In contrast, when a zinc finger protein is administered in vivo for gene regulation, either a constitutive or an inducible promoter is used, depending on the particular use of the zinc finger protein. The promoter typically can also include elements that are responsive to transactivation, e.g., hypoxia response elements, Gal4 response elements, lac repressor response element, and small molecule control systems such as tet-regulated systems and the RU-486 system (see, e.g., Gossen & Bujard, *Proc. Natl. Acad. Sci. U.S.A.* 89:5547 (1992); Oligino et al., *Gene Ther.* 5:491–496 (1998); Wang et al., *Gene Ther.* 4:432–441 (1997); Neering et al., *Blood* 88:1147–1155 (1996); and Rendahl et al., *Nat. Biotechnol.* 16:757–761(1998)).

In addition to the promoter, the expression vector typically contains a transcription unit or expression cassette that contains all the additional elements required for the expression of the nucleic acid in host cells, either prokaryotic or eukaryotic. A typical expression cassette thus contains a promoter operably linked, e.g., to the nucleic acid sequence encoding the zinc finger protein, and signals required, e.g., for efficient polyadenylation of the transcript, transcriptional termination, ribosome binding sites, or translation termination. Additional elements of the cassette may include, e.g., enhancers, and heterologous spliced intronic signals.

The particular expression vector used to transport the genetic information into the cell is selected with regard to the intended use of the zinc finger protein, e.g., expression in plants, animals, bacteria, fungus, protozoa etc. (see expression vectors described below and in the Example section). Standard bacterial expression vectors include plasmids such as pBR322 based plasmids, pSKF, pET23D, and commercially available fusion expression systems such as GST and LacZ. A preferred fusion protein is the maltose binding protein, "MBP." Such fusion proteins are used for purification of the zinc finger protein. Epitope tags can also be added to recombinant proteins to provide convenient methods of isolation, for monitoring expression, and for monitoring cellular and subcellular localization, e.g., c-myc or FLAG.

Expression vectors containing regulatory elements from eukaryotic viruses are often used in eukaryotic expression vectors, e.g., SV40 vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the SV40 early promoter, SV40 late promoter, CMV promoter, metallothionein promoter, murine mammary tumor virus promoter, Rous sarcoma virus promoter, polyhedrin promoter, or other promoters shown effective for expression in eukaryotic cells.

Some expression systems have markers for selection of stably transfected cell lines such as neomycin, thymidine kinase, hygromycin B phosphotransferase, and dihydrofolate reductase. High yield expression systems are also suitable, such as using a baculovirus vector in insect cells, with a zinc finger protein encoding sequence under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of recombinant sequences.

Standard transfection methods are used to produce bacterial, mammalian, yeast or insect cell lines that express large quantities of protein, which are then purified using standard techniques (see, e.g., Colley et al., *J. Biol. Chem.* 264:17619–17622 (1989); *Guide to Protein Purification, in Methods in Enzymology,* vol. 182 (Deutscher, ed., 1990)). Transformation of eukaryotic and prokaryotic cells are performed according to standard techniques (see, e.g., Morrison, *J. Bact.* 132:349–351 (1977); Clark-Curtiss & Curtiss, *Methods in Enzymology* 101:347–362 (Wu et al., eds, 1983).

Any of the well known procedures for introducing foreign nucleotide sequences into host cells may be used. These include the use of calcium phosphate transfection, polybrene, protoplast fusion, electroporation, liposomes, microinjection, naked DNA, plasmid vectors, viral vectors, both episomal and integrative, and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing the protein of choice.
Vectors Encoding Zinc Finger Proteins for Regulation of Gene Expression Conventional viral and non-viral based gene transfer methods can be used to introduce nucleic acids encoding engineered zinc finger protein in mammalian cells or target tissues. Such methods can be used to administer nucleic acids encoding zinc finger proteins to cells in vitro or in vivo. Non-viral vector delivery systems include DNA plasmids, naked nucleic acid, and nucleic acid complexed with a delivery vehicle such as a liposome. Viral vector delivery systems include DNA and RNA viruses, which have either episomal or integrated genomes after delivery to the cell. For a review of gene therapy procedures, see Anderson, Science 256:808–813 (1992); Nabel & Felgner, TIBTECH 11:211–217 (1993); Mitani & Caskey, TIBTECH 11:162–166 (1993); Dillon, TIBTECH 11:167–175 (1993); Miller, Nature 357:455–460 (1992); Van Brunt, Biotechnology 6(10):1149–1154 (1988); Vigne, Restorative Neurology and Neuroscience 8:35–36 (1995); Kremer & Perricaudet, British Medical Bulletin 51(1):3 1–44 (1995); Haddada et al., in Current Topics in Microbiology and Immunology Doerfler and Bohm (eds) (1995); and Yu et al., Gene Therapy 1:13–26 (1994).

Methods of non-viral delivery of nucleic acids encoding engineered zinc finger proteins include lipofection, microinjection, biolistics, virosomes, liposomes, immunoliposomes, polycation or lipid:nucleic acid conjugates, naked DNA, artificial virions, and agent-enhanced uptake of DNA. Lipofection is described in e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424, WO 91/16024. Delivery can be to cells (ex vivo administration) or target tissues (in vivo administration).

The preparation of lipid:nucleic acid complexes, including targeted liposomes such as immunolipid complexes, is well known to one of skill in the art (see, e.g., Crystal, Science 270:404–410 (1995); Blaese et al., Cancer Gene Ther. 2:291–297 (1995); Behr et al., Bioconjugate Chem. 5:382–389 (1994); Remy et al., Bioconjugate Chem. 5:647–654 (1994); Gao et al., Gene Therapy 2:710–722 (1995); Ahmad et al., Cancer Res. 52:4817–4820 (1992); U.S. Pat. Nos. 4,186,183, 4,217,344, 4,235,871, 4,261,975, 4,485,054, 4,501,728, 4,774,085, 4,837,028, and 4,946,787).

The use of RNA or DNA viral based systems for the delivery of nucleic acids encoding engineered zinc finger protein take advantage of highly evolved processes for targeting a virus to specific cells in the body and trafficking the viral payload to the nucleus. Viral vectors can be administered directly to subjects (in vivo) or they can be used to treat cells in vitro and the modified cells are administered to patients (ex vivo). Conventional viral based systems for the delivery of zinc finger proteins could include retroviral, lentivirus, adenoviral, adeno-associated and herpes simplex virus vectors for gene transfer. Viral vectors are currently the most efficient and versatile method of gene transfer in target cells and tissues. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vector that are able to transduce or infect non-dividing cells and typically produce high viral titers. Selection of a retroviral gene transfer system would therefore depend on the target tissue. Retroviral vectors are comprised of cis-acting long terminal repeats with packaging capacity for up to 6–10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), simian immuno-deficiency virus (SIV), human immuno-deficiency virus (HIV), and combinations thereof (see, e.g., Buchscher et al., J. Virol. 66:2731–2739 (1992); Johann et al., J. Virol. 66:1635–1640 (1992); Sommerfelt et al., Virol. 176:58–59 (1990); Wilson et al., J. Virol. 63:2374–2378 (1989); Miller et al., J. Virol. 65:2220–2224 (1991); PCT/US94/05700).

In applications where transient expression of the zinc finger protein is preferred, adenoviral based systems are typically used. Adenoviral based vectors are capable of very high transduction efficiency in many cell types and do not require cell division. With such vectors, high titer and levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al, Virology 160:38–47 (1987); U.S. Pat. No. 4,797,368; WO 93/24641; Kotin, Human Gene Therapy 5:793–801 (1994); Muzyczka, J. Clin. Invest. 94:1351 (1994). Construction of recombinant AAV vectors are described in a number of publications, including U.S. Pat. No. 5,173,414; Tratschin et al., Mol. Cell. Biol. 5:3251–3260 (1985); Tratschin, et al., Mol. Cell. Biol. 4:2072–2081 (1984); Hermonat & Muzyczka, Proc. Natl. Acad. Sci. U.S.A. 81:6466–6470 (1984); and Samulski et al., J. Virol. 63:03822–3828 (1989).

Packaging cells are used to form virus particles that are capable of infecting a host cell. Such cells include 293 cells, which package adenovirus, and ψ2 cells or PA317 cells, which package retrovirus. Viral vectors used in gene therapy are usually generated by producer cell line that packages a nucleic acid vector into a viral particle. The vectors typically contain the minimal viral sequences required for packaging and subsequent integration into a host, other viral sequences being replaced by an expression cassette for the protein to be expressed. The missing viral functions are supplied in trans by the packaging cell line. For example, AAV vectors used in gene therapy typically only possess ITR sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many situations, it is desirable that the vector be delivered with a high degree of specificity to a particular tissue type. A viral vector is typically modified to have specificity for a given cell type by expressing a ligand as a fusion protein with a viral coat protein on the viruses outer surface. The ligand is chosen to have affinity for a receptor known to be present on the cell type of interest. For example, Han et al., *Proc. Natl. Acad. Sci. U.S.A.* 92:9747–9751 (1995), reported that Moloney murine leukemia virus can be modified to express human hereguiin fused to gp70, and the recombinant virus infects certain human breast cancer cells expressing human epidermal growth factor receptor. This principle can be extended to other pairs of virus expressing a ligand fusion protein and target cell expressing a receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences thought to favor uptake by specific target cells.

Expression vectors can be delivered in vivo by administration to an individual subject, typically by systemic administration (e.g., intravenous, intraperitoneal, intramuscular, subdermal, or intracranial infusion) or topical application, as described below. Alternatively, naked DNA can be administered. Alternatively, vectors can be delivered to cells ex vivo, such as cells explanted from an individual subject (e.g., lymphocytes, bone marrow aspirates, tissue biopsy) or universal donor hematopoietic stem cells, followed by reimplantation of the cells into a patient, usually after selection for cells which have incorporated the vector.

Administration is by any of the routes normally used for introducing a molecule into ultimate contact with blood or tissue cells. Suitable methods of administering such nucleic acids are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention, as described below (see, e.g., *Remington's Pharmaceutical Sciences,* 17th ed., 1989).

Delivery Vehicles for Zinc Finger Proteins

An important factor in the administration of polypeptide compounds, such as the zinc finger proteins, is ensuring that the polypeptide has the ability to traverse the plasma membrane of a cell, or the membrane of an intra-cellular compartment such as the nucleus. Cellular membranes are composed of lipid-protein bilayers that are freely permeable to small, nonionic lipophilic compounds and are inherently impermeable to polar compounds, macromolecules, and therapeutic or diagnostic agents. However, proteins and other compounds such as liposomes have been described, which have the ability to translocate polypeptides such as zinc finger proteins across a cell membrane.

For example, "membrane translocation polypeptides" have amphiphilic or hydrophobic amino acid subsequences that have the ability to act as membrane-translocating carriers. In one embodiment, homeodomain proteins have the ability to translocate across cell membranes. The shortest internalizable peptide of a homeodomain protein, Antennapedia, was found to be the third helix of the protein, from amino acid position 43 to 58 (see, e.g., Prochiantz, *Current Opinion in Neurobiology* 6:629–634 (1996)). Another subsequence, the h (hydrophobic) domain of signal peptides, was found to have similar cell membrane translocation characteristics (see, e.g., Lin et al., *J. Biol. Chem.* 270:1 4255–14258 (1995)).

Examples of peptide sequences which can be linked to a zinc finger protein of the invention, for facilitating uptake of zinc finger protein into cells, include, but are not limited to: an 11 amino acid peptide of the tat protein of HIV; a 20 residue peptide sequence which corresponds to amino acids 84–103 of the p16 protein (see Fahraeus et al., *Current Biology* 6:84 (1996)); the third helix of the 60-amino acid long homeodomain of Antennapedia (Derossi et al., *J. Biol. Chem.* 269:10444 (1994)); the h region of a signal peptide such as the Kaposi fibroblast growth factor (K-FGF) h region (Lin et al., supra); or the VP22 translocation domain from HSV (Elliot & O'Hare, *Cell* 88:223–233 (1997)). Other suitable chemical moieties that provide enhanced cellular uptake may also be chemically linked to zinc finger proteins.

Toxin molecules also have the ability to transport polypeptides across cell membranes. Often, such molecules are composed of at least two parts (called "binary toxins"): a translocation or binding domain or polypeptide and a separate toxin domain or polypeptide. Typically, the translocation domain or polypeptide binds to a cellular receptor, and then the toxin is transported into the cell. Several bacterial toxins, including *Clostridium perfringens* iota toxin, diphtheria toxin (DT), Pseudomonas exotoxin A (PE), pertussis toxin (PT), *Bacillus anthracis* toxin, and pertussis adenylate cyclase (CYA), have been used in attempts to deliver peptides to the cell cytosol as internal or amino-terminal fusions (Arora et al., *J. Biol. Chem.,* 268:3334–3341 (1993); Perelle et al., *Infect. Immun.,* 61:5147–5156 (1993); Stenmark et al., *J. Cell Biol.* 113:1025–1032 (1991); Donnelly et al., *Proc. Natl. Acad. Sci. U.S.A.* 90:3530–3534 (1993); Carbonetti et al., *Abstr. Annu. Meet. Am. Soc. Microbiol.* 95:295 (1995); Sebo et al., *Infect. Immun.* 63:3851–3857 (1995); Klimpel et al., *Proc. Natl. Acad. Sci. U.S.A.* 89:10277–10281 (1992); and Novak et al., *J. Biol. Chem.* 267:17186–17193 1992)).

Such subsequences can be used to translocate zinc finger proteins across a cell membrane. zinc finger proteins can be conveniently fused to or derivatized with such sequences. Typically, the translocation sequence is provided as part of a fusion protein. Optionally, a linker can be used to link the zinc finger protein and the translocation sequence. Any suitable linker can be used, e.g., a peptide linker.

The zinc finger protein can also be introduced into an animal cell, preferably a mammalian cell, via a liposomes and liposome derivatives such as immunoliposomes. The term "liposome" refers to vesicles comprised of one or more concentrically ordered lipid bilayers, which encapsulate an aqueous phase. The aqueous phase typically contains the compound to be delivered to the cell, i.e., a zinc finger protein.

The liposome fuses with the plasma membrane, thereby releasing the drug into the cytosol. Alternatively, the liposome is phagocytosed or taken up by the cell in a transport vesicle. Once in the endosome or phagosome, the liposome either degrades or fuses with the membrane of the transport vesicle and releases its contents.

In current methods of drug delivery via liposomes, the liposome ultimately becomes permeable and releases the encapsulated compound (in this case, a zinc finger protein) at the target tissue or cell. For systemic or tissue specific delivery, this can be accomplished, for example, in a passive manner wherein the liposome bilayer degrades over time through the action of various agents in the body. Alternatively, active drug release involves using an agent to induce a permeability change in the liposome vesicle. Liposome membranes can be constructed so that they become destabilized when the environment becomes acidic near the liposome membrane (see, e.g., *Proc. Natl. Acad. Sci. U.S.A.* 84:7851 (1987); *Biochemistry* 28:908 (1989)). When liposomes are endocytosed by a target cell, for example, they become destabilized and release their contents. This destabilization is termed fusogenesis. Dioleoylphosphatidylethanolamine (DOPE) is the basis of many "fusogenic" systems.

Such liposomes typically comprise a zinc finger protein and a lipid component, e.g., a neutral and/or cationic lipid, optionally including a receptor-recognition molecule such as an antibody that binds to a predetermined cell surface receptor or ligand (e.g., an antigen). A variety of methods are available for preparing liposomes as described in, e.g., Szoka et al., *Ann. Rev. Biophys. Bioeng.* 9:467 (1980), U.S. Pat. Nos. 4,186,183, 4,217,344, 4,235,871, 4,261,975, 4,485,054, 4,501,728, 4,774,085, 4,837,028, 4,235,871, 4,261,975, 4,485,054, 4,501,728, 4,774,085, 4,837,028, 4,946,787, PCT Publication No. WO 91\17424, Deamer & Bangham, *Biochim. Biophys. Acta* 443:629–634 (1976); Fraley, et al., *Proc. Natl. Acad. Sci. U.S.A.* 76:3348–3352 (1979); Hope et al., *Biochim. Biophys. Acta* 812:55–65 (1985); Mayer et al., *Biochim. Biophys. Acta* 858:161–168 (1986); Williams et al., *Proc. Natl. Acad. Sci. U.S.A.* 85:242–246 (1988); Liposomes (Ostro (ed.), 1983, Chapter 1); Hope et al., *Chem. Phys. Lip.* 40:89 (1986); Gregoriadis, *Liposome Technology* (1984) and Lasic, *Liposomes: from Physics to Applications* (1993)). Suitable methods include, for example, sonication, extrusion, high pressure/homogenization, microfluidization, detergent dialysis, calcium-induced fusion of small liposome vesicles and ether-fusion methods, all of which are well known in the art.

In certain embodiments of the present invention, it is desirable to target the liposomes of the invention using targeting moieties that are specific to a particular cell type, tissue, and the like. Targeting of liposomes using a variety of targeting moieties (e.g., ligands, receptors, and monoclonal antibodies) has been previously described (see, e.g., U.S. Pat. Nos. 4,957,773 and 4,603,044).

Examples of targeting moieties include monoclonal antibodies specific to antigens associated with neoplasms, such as prostate cancer specific antigen and MAGE. Tumors can also be diagnosed by detecting gene products resulting from the activation or over-expression of oncogenes, such as ras or c-erbB2. In addition, many tumors express antigens normally expressed by fetal tissue, such as the alphafetoprotein (AFP) and carcinoembryonic antigen (CEA). Sites of viral infection can be diagnosed using various viral antigens such as hepatitis B core and surface antigens (HBVc, HBVs) hepatitis C antigens, Epstein-Barr virus antigens, human immunodeficiency type-1 virus (HIV1) and papilloma virus antigens. Inflammation can be detected using molecules specifically recognized by surface molecules which are expressed at sites of inflammation such as integrins (e.g., VCAM-1), selectin receptors (e.g., ELAM-1) and the like.

Standard methods for coupling targeting agents to liposomes can be used. These methods generally involve incorporation into liposomes lipid components, e.g., phosphatidylethanolamine, which can be activated for attachment of targeting agents, or derivatized lipophilic compounds, such as lipid derivatized bleomycin. Antibody targeted liposomes can be constructed using, for instance, liposomes which incorporate protein A (see Renneisen et al., *J. Biol. Chem.*, 265:16337–16342 (1990) and Leonetti et al., *Proc. Natl. Acad. Sci. U.S.A.* 87:2448–2451 (1990).

Assays for Determining Regulation of Gene Expression by Zinc Finger Proteins

A variety of assays can be used to determine association of a candidate gene with a selected phenotype. The activity of a particular gene regulated by a zinc finger protein can be assessed using a variety of in vitro and in vivo assays, by measuring, e.g., protein or mRNA levels, product levels, enzyme activity, tumor growth; transcriptional activation or repression of a reporter gene; second messenger levels (e.g., cGMP, cAMP, IP3, DAG, $Ca^{2+}$); cytokine and hormone production levels; and neovascularization, using, e.g., immunoassays (e.g., ELISA and immunohistochemical assays with antibodies), hybridization assays (e.g., RNase protection, notherns, in situ hybridization, oligonucleotide array studies), calorimetric assays, amplification assays, enzyme activity assays, tumor growth assays, phenotypic assays, cDNA arrays studies, and the like.

Zinc finger proteins are often first tested for activity in vitro using cultured cells, e.g., 293 cells, CHO cells, VERO cells, BHK cells, HeLa cells, COS cells, and the like. Preferably, human or mouse cells are used. The zinc finger protein is often first tested using a transient expression system with a reporter gene, and then regulation of the target candidate gene is tested in cells and in animals, both in vivo and ex vivo. The zinc finger protein can be recombinantly expressed in a cell, recombinantly expressed in cells transplanted into an animal, or recombinantly expressed in a transgenic animal, as well as administered as a protein to an animal or cell using delivery vehicles described below. The cells can be immobilized, be in solution, be injected into an animal, or be naturally occurring in a transgenic or non-transgenic animal.

Modulation of gene expression and association of the candidate gene with a selected phenotype is tested using one of the in vitro or in vivo assays described herein. Cells or subject animals comprising the candidate genes are contacted with zinc finger proteins and compared to control genes or second candidate genes to examine the extent of phenotype modulation. For regulation of gene expression, the zinc finger protein optionally has a $K_d$ of 200 nM or less, more preferably 100 nM or less, more preferably 50 nM, most preferably 25 nM or less.

The effects of the zinc finger proteins can be measured by examining any of the parameters described above. Any suitable gene expression, phenotypic, or physiological change can be used to assess the influence of a zinc finger protein. When the functional consequences are determined using intact cells or animals, one can also measure a variety of effects such as tumor growth, neovascularization, hormone release, transcriptional changes to both known and uncharacterized genetic markers (e.g., northern blots or oligonucleotide array studies), changes in cell metabolism such as cell growth or pH changes, and changes in intracellular second messengers such as cGMP.

Examples of assays for a selected phenotype include e.g., transformation assays, e.g., changes in proliferation, anchorage dependence, growth factor dependence, foci formation, growth in soft agar, tumor proliferation in nude mice, and tumor vascularization in nude mice; apoptosis assays, e.g., DNA laddering and cell death, expression of genes involved in apoptosis; signal transduction assays, e.g., changes in intracellular calcium, cAMP, cGOMP, IP3, changes in hormone and neurotransmitter release; receptor assays, e.g., estrogen receptor and cell growth; growth factor assays, e.g., EPO, hypoxia and erythrocyte colony forming units assays; enzyme product assays, e.g., FAD-2 induced oil desaturation; transcription assays, e.g., reporter gene assays; and protein production assays, e.g., VEGF ELISAs.

In one embodiment, the assay for the selected phenotype is performed in vitro. In one preferred in vitro assay format, zinc finger protein regulation of gene expression in cultured cells is examined by determining protein production using an ELISA assay.

In another embodiment, zinc finger protein regulation of candidate gene expression is determined in vitro by measuring the level of target gene mRNA expression. The level of gene expression is measured using amplification, e.g., using PCR, LCR, or hybridization assays, e.g., northern hybridization, RNase protection, dot blotting. RNase protection is used in one embodiment. The level of protein or mRNA is detected using directly or indirectly labeled detection agents, e.g., fluorescently or radioactively labeled nucleic acids, radioactively or enzymatically labeled antibodies, and the like, as described herein.

Alternatively, a reporter gene system can be devised using a target gene promoter operably linked to a reporter gene such as luciferase, green fluorescent protein, CAT, or β-gal. The reporter construct is typically co-transfected into a cultured cell. After treatment with the zinc finger protein of choice, the amount of reporter gene transcription, translation, or activity is measured according to standard techniques known to those of skill in the art.

Another example of an assay format useful for monitoring zinc finger protein regulation of candidate gene expression is performed in vivo. This assay is particularly useful for examining zinc finger proteins that inhibit expression of tumor promoting genes, genes involved in tumor support, such as neovascularization (e.g., VEGF), or that activate tumor suppressor genes such as p53. In this assay, cultured tumor cells expressing the zinc finger protein of choice are injected subcutaneously into an immune compromised mouse such as an athymic mouse, an irradiated mouse, or a SCID mouse. After a suitable length of time, preferably 4–8 weeks, tumor growth is measured, e.g., by volume or by its two largest dimensions, and compared to the control. Tumors that have statistically significant reduction (using, e.g., Student's T test) are said to have inhibited growth. Alternatively, the extent of tumor neovascularization can also be measured. Immunoassays using endothelial cell specific antibodies are used to stain for vascularization of the tumor and the number of vessels in the tumor. Tumors that have a statistically significant reduction in the number of vessels (using, e.g., Student's T test) are said to have inhibited neovascularization.

Transgenic and non-transgenic animals are also used as an embodiment for examining regulation of candidate gene expression in vivo. Transgenic animals typically express the zinc finger protein of choice. Alternatively, animals that transiently express the zinc finger protein of choice, or to which the zinc finger protein has been administered in a delivery vehicle, can be used. Regulation of candidate gene expression is tested using any one of the assays described herein. Animals can be observed and assayed for functional changes, e.g., challenged with drugs, mitogens, viruses, pathogens, toxins, and the like.

Transgenic Mice and in Vitro Throughput Assays for Drug Discovery

A further application of the zinc finger protein technology is manipulating gene expression in cell lines and transgenic animals. Once a selected candidate gene has been associated with a phenotype, and the candidate gene has been validated as a drug therapy target, cell and transgenic-animal based assays are developed for the purposes of high throughput drug screening. A cell line or animal expressing the candidate gene is provided with a zinc finger protein that regulates expression of the candidate gene. The zinc finger protein typically is provided as a nucleic acid encoding the zinc finger protein, although it can also be administered as a protein. The cell line or animal is then contacted with test compounds to determine the effect of the compound upon the candidate gene and the selected phenotype. The zinc finger protein technology is an improvement for high throughput cell-based and animal assays, for example, because expression of the zinc finger protein can be made conditional using small molecule systems.

In one embodiment of a high throughput assay for therapeutics, zinc finger proteins can be used for regulation of candidate genes in cell lines or animals using the small molecule regulated systems described herein. Expression and/or function of a zinc finger-based repressor can be switched off during development and switched on at will in the cells or animals. This approach relies on the addition of the zinc finger protein expressing module only; homologous recombination is not required. Because the zinc finger protein repressors are trans dominant, there is no concern about germline transmission or homozygosity. These issues dramatically affect the time and labor required to go from a poorly characterized gene candidate (a cDNA or EST clone) to a mouse model. This ability can be used to rapidly identify and/or validate gene targets for therapeutic intervention, generate novel model systems and permit the analysis of complex physiological phenomena (development, hematopoiesis, transformation, neural function etc.). Chimeric targeted mice can be derived according to Hogan et al., *Manipulating the Mouse Embryo: A Laboratory Manual,* (1988); *Teratocarcinomas and Embryonic Stem Cells: A Practical Approach,* Robertson, ed., (1987); and Capecchi et al., *Science* 244:1288 (1989.

Doses of Zinc Finger Proteins

The dose administered to a subject or a cell, in the context of the present invention should be sufficient to effect the desired phenotype. Particular dosage regimens can be useful for determining phenotypic changes in an experimental setting, e.g., in functional genomics studies, and in cell or animal models. The dose is determined by the efficacy and $K_d$ of the particular zinc finger protein employed, the nuclear volume of the target cell, and the condition of the cell or patient, as well as the body weight or surface area of the cell or patient to be treated. The size of the dose also is determined by the existence, nature, and extent of any adverse side-effects that accompany the administration of a particular compound or vector in a particular cell or patient.

The maximum effective dosage of zinc finger protein for approximately 99% binding to target sites is calculated to be in the range of less than about $1.5 \times 10^5$ to $1.5 \times 10^6$ copies of the specific zinc finger protein molecule per cell. The number of zinc finger proteins per cell for this level of binding is calculated as follows, using the volume of a HeLa cell nucleus (approximately 1000 $\mu m^3$ or $10^{-12}$ L; *Cell Biology,* (Altman & Katz, eds. (1976)). As the HeLa nucleus is relatively large, this dosage number is recalculated as needed using the volume of the target cell nucleus. This calculation also does not take into account competition for zinc finger protein binding by other sites. This calculation also assumes that essentially all of the zinc finger protein is localized to the nucleus. A value of $100 \times K_d$ is used to calculate approximately 99% binding of to the target site, and a value of $10 \times K_d$ is used to calculate approximately 90% binding of to the target site. For this example, $K_d=25$ nM ZFP+target site⇌complex i.e., DNA+protein⇌DNA:protein complex $K_d$=[DNA] [protein] [DNA:protein complex]

When 50% of ZFP is bound, $K_d$=[protein]

So when [protein]=25 nM and the nucleus volume is $10^{-12}$ L [protein]=$(25 \times 10^{-9}$ moles/L) $(10^{-12}$ L/nucleus) $(6 \times 10^{23}$ molecules/mole)=15,000 molecules/nucleus for 50% binding When 99% target is bound; $100 \times K_d$=[protein]$100 \times K_d$=[protein]= 2.5 μM $(2.5 \times 10^{-6}$ moles/L) $(10^{-12}$L/nucleus) $(6 \times 10^{23}$ molecules/mole)= about 1,500,000 molecules per nucleus for 99% binding of target site.

The appropriate dose of an expression vector encoding a zinc finger protein can also be calculated by taking into account the average rate of zinc finger protein expression from the promoter and the average rate of zinc finger protein degradation in the cell. Preferably, a weak promoter such as a wild-type or mutant HSV TK is used, as described above. The dose of zinc finger protein in micrograms is calculated by taking into account the molecular weight of the particular zinc finger protein being employed.

In determining the effective amount of the zinc finger protein to be administered, circulating plasma levels of the zinc finger protein or nucleic acid encoding the zinc finger protein, potential zinc finger protein toxicities, progression of the phenotype, and the production of anti-zinc finger protein antibodies are evaluated. Administration can be accomplished via single or divided doses.

Pharmaceutical Compositions and Administration

Zinc finger proteins and expression vectors encoding zinc finger proteins can be administered directly to the subject or cell for modulation of gene expression. Administration of effective amounts is by any of the routes normally used for introducing zinc finger protein into ultimate contact with the tissue or cell. The zinc finger proteins are administered in any suitable manner, preferably with pharmaceutically acceptable carriers. Suitable methods of administering such modulators are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention (see, e.g., *Remington's Pharmaceutical Sciences*, 17$^{th}$ ed. 1985)).

The zinc finger proteins, nucleic acids encoding the same, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intravenous, intramuscular, intradermal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. The formulations of compounds can be presented in unit-dose or multi-dose sealed containers, such as ampules and vials. Injection solutions and suspensions can be prepared from sterile powders, granules, and tablets of the kind previously described.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

EXAMPLES

The following examples are provided by way of illustration only and not by way of limitation. Those of skill in the art will readily recognize a variety of noncritical parameters that could be changed or modified to yield essentially similar results.

Example I

Targeting Human VEGF Gene with Zinc Finger Proteins for Target Validation

An important consideration in target validation is to efficiently determine and accurately evaluate the relationship between a targeted gene and resulting phenotype. This example demonstrates the use of the zinc finger protein technology to validate a gene as a target for the development of therapeutic compounds that can regulate, e.g., expression of the gene or the function of the gene product. This process is based on the following simple assumptions (FIG. 1).

If a gene X is up-regulated by a ZFP-A1, which specifically targets at the X1 site, a phenotype Q is observed.

If the gene X is up-regulated by ZFP-A2, which specifically targets at a different site X2, the same phenotype Q should be observed.

If the gene X is down-regulated by ZFP-B1, which targets at the X3 site (X3 can be X1 or X2), a different phenotype Z should be observed.

If the ZFP-A1, ZFP-A2, or ZFP-B1 are used to target a gene that is not involved in the phenotype Q, no phenotype change related to this gene should be observed.

The human and mouse vascular endothelial growth factor (VEGF) genes were selected for target validation in this example. VEGF is an approximately 46 kDa glycoprotein that is an endothelial cell-specific mitogen induced by hypoxia. VEGF binds to endothelial cells via interaction with tyrosine kinase receptors Flt-1 (VEGFR- 1) and Flk-1/KDR (VEGFR-2). Since VEGF plays a very important role in angiogenesis, targeting this gene for development of therapeutics has attracted great interest. While inhibition (down-regulation) of the VEGF gene may be used for cancer and diabetic retinopathy treatments, activation (up-regulation) of the gene may be used for ischemic heart and tissue diseases. These two desired phenotypic changes make the VEGF gene ideal for target validation using zinc finger protein technology.

Testing Zinc Finger Proteins for Biochemical Affinity and Specificity in vitro

The DNA target sites for zinc finger proteins were chosen in a region surrounding the transcription site of the targeted gene. The primary targets were chosen within the region approximately 1 kb upstream of the transcription initiation site, where a majority of enhancer elements are located. Each 3-finger zinc finger protein recognizes a 9-bp DNA sequence. To increase DNA-binding specificity, two 3-finger zinc finger proteins are fused together in order to target two 9-bp DNA sequences that are in a close proximity (Liu et al. *Proc. Natl. Acad. Sci. U.S.A.* 94:5525–5530 (1997)).

Human SP-1 or murine Zif268 transcription factors were used as a progenitor molecular for the construction of designed zinc finger proteins. The amino acid sequences (fingers), which recognize the target DNA sequence, were designed based on the "recognition rules" described herein. The designed zinc finger protein genes were constructed using a PCR-based procedure that utilizes six overlapping oligonucleotides. The methods of designing and assembling zinc finger protein genes that target VEGF are detailed in U.S. Ser. No. 09/229,037.

Figure 2:
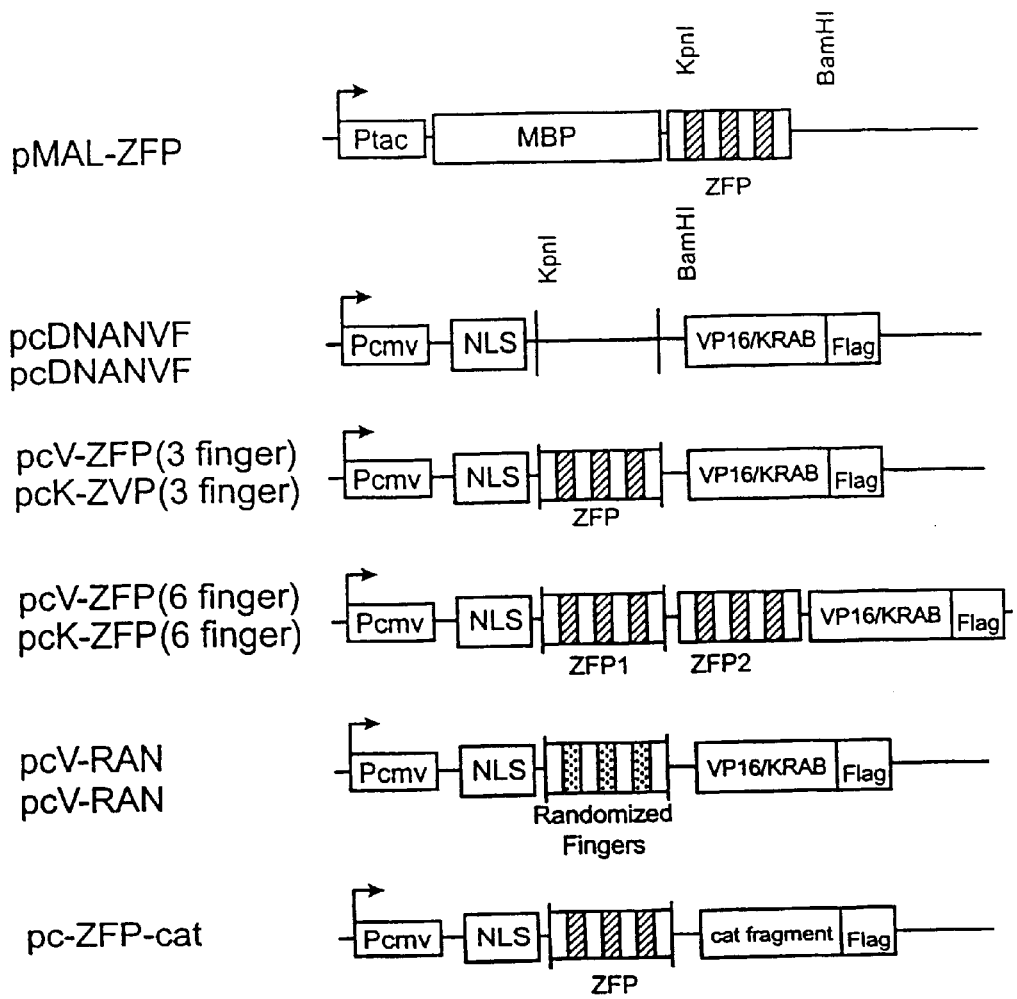
FIG. 2 shows zinc finger protein expression constructs.

The designed zinc finger protein genes were initially cloned into the pMAL-KNB vector after digesting with KpnI and BamHI (FIG. 2). The pMAL-KNB vector is modified from the pMAL-c2 vector (New England Biolabs, MA). The zinc finger protein proteins were purified from bacteria and were subjected to biochemical affinity and specificity assays. The methods for these in vitro assays are described herein and in co-pending application U.S. Ser. No. 09/229,037.

Activation or Repression of a Luciferase Promoter in Transiently Transfected Cells The zinc finger proteins with high biochemical affinity and specificity were subcloned into the KpnI and BamHI sites in pcDNA-NVF or pcDNA-NKF (FIG. 2). The pcDNA-NVF construct contains a CMV promoter-controlled sequence encoding a nuclear localization signal, a herpes simplex virus VP16 activation domain, and a Flag peptide. This construct was designed to up-regulate the targeted gene when introduced into mammalian cells. The pcDNA-NKF construct contains the Kruppel-associated box (KRAB) repression domain instead of VP16 domain and was used for down-regulation of the targeted genes. These constructs are described in detail in co-pending application U.S. Ser. No. 09/229,037.

Figure 3:
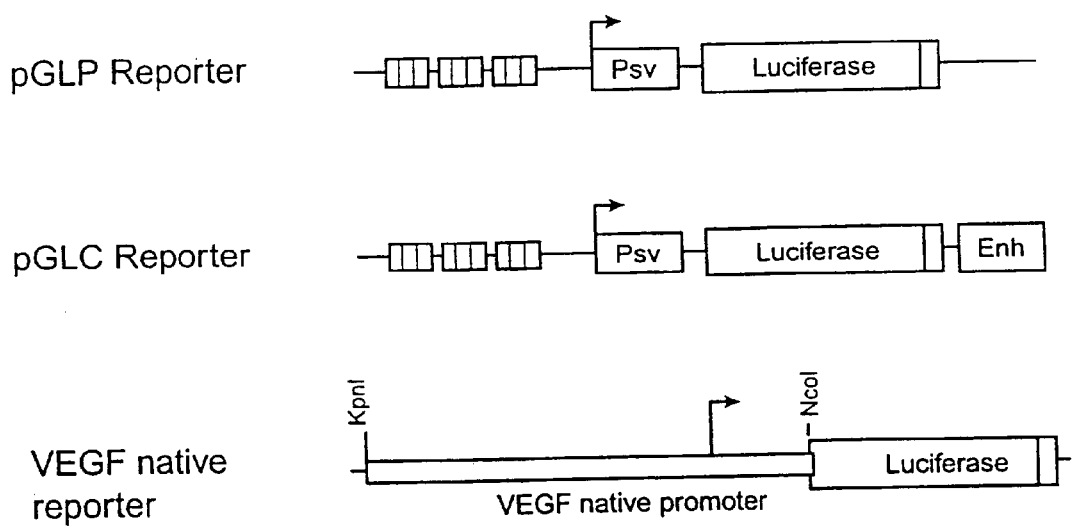
FIG. 3 shows luciferase reporter constructs for zinc finger protein regulation of gene expression.

The reporter plasmid system is based on the pGL3-promoter and pGL3-control vectors (Promega, WI). Three tandem repeats of the zinc finger protein target sites were inserted upstream of the SV40 promoter (FIG. 3). The pGLP reporters were used to evaluate the activities of the engineered zinc finger proteins for up-regulation of gene expression and the pGLC reporters were used to measure the effects of ZFP-KRAB activities inhibition of gene expression. These constructs are described in detail in co-pending U.S. Ser. No. 09/229,037.

The control plasmids used in this example are shown in FIG. 2. pcDNA-NVF (or pcDNA-NKF) is a ZFP-less effector. pcV-RAN (or pcK-RAN) expresses all components except that the engineered zinc finger protein has no known DNA binding capability (FIG. 2). The zinc finger protein sequence in the pcV-RAN (or pcK-RAN) constructs is:

V P G K K K Q H I C H I Q G C G K V Y G <u>GHDTVVGHLRWHTGERPFMCTWSYCGKRT AADEVGLHKRTHTGEKKFACPECPKRFM LVVATQLHIKTHQNKKGGS</u> (SEQ ID NO:13), where the fingers are underlined. These control constructs were used to check the effects of the regulation domains (VP16 or KRAB), in the absence of the DNA binding domain. The pc-ZFP-cat plasmid expresses a specifically designed zinc finger protein, however the functional domain (VP16 or KRAB) was replaced with a 234 bp fragment isolated from the chloramphenicol acetyltransferase (CAT) gene in the pcDNA3.1/CAT vector (nt1442 to 1677) (Invitrogen, CA) (FIG. 2). This control plasmid was used to test whether the DNA binding domain alone has any effects on gene expression. The other controls include effectors expressing zinc finger proteins that recognize different DNA sequences and reporters containing non-specific zinc finger protein target sequences.

The following example demonstrates the effect of a designed zinc finger protein, which activates the luciferase reporter gene in 293 cells. The targeted sequence, GGGGTTGAG, is named M6-1 892S and is in the promoter region of the human VEGF gene. The zinc finger protein recognizing this 9-bp DNA sequence was designed and assembled as described herein and in U.S. Ser. No. 09/229, 037. The DNA sequence (SEQ ID NO:14) and the amino acid sequence (SEQ ID NO:15) of the zinc finger protein are shown below.

```
                    KpnI
5' GGTACCGGGCAAGAAGAAGCAGCACATCTGCCACATCCAGGGCTGTGGTAAAGTT

V  P  G  K  K  K  Q  H  I  C  H  I  Q  G  C  G  K  V

TACGGCCGCTCCGACAACCTGACCCGCCACCTGCGCTGGCACACCGGCGAGAGGCCT

Y  G  R  S  D  N  L  T  R  H  L  R  W  H  T  G  E  R  P (Finger 1: GAG)

TTCATGTGTACATGGTCCTACTGTGGTAAACGCTTCACCAACCGCGACACCCTGGCC

F  M  C  T  W  S  Y  C  G  K  R  F  T  N  R  D  T  L  A (Finger 2: GTT)
```

```
CGCCACAAGCGTACCCACACCGGTGAGAAGAAATTTGCTTGTCCGGAATGTCCGAAG

R   H   K   R   T   H   T   G   E   K   K   F   A   C   P   E   C   P   K

CGCTTCATGCGCTCCGACCACCTGTCCAAGCACATCAAGACCCACCAGAACAAGAAG

R   F   M   R   S   D   H   L   S   K   H   I   K   T   H   Q   N   K   K
 ‾       ‾   ‾   ‾   ‾   ‾   ‾   ‾   ‾

(Finger 3: GGG)

GGTGGATCC-3'
   ‾‾‾‾‾
 G   G   S

BamHI
```

The KpnI-BamHI DNA fragment of the assembled zinc finger protein was cloned into KpnI-BamHI sites of the pMAL-KNB vector. The ability of the designed zinc finger proteins to bind their target sites was verified by expressing and purifying recombinant proteins from *E. coli* and performing electrophoretic mobility shift assays (EMSA). The binding affinity ($K_d$) of the protein shown above was 20 nM, as determined by EMSA. This KpnI-BamHI ZFP fragment was then subcloned into KpnI-BamHI sites of the pcDNA-NVF vector and was named pcV-VF471A. The luciferase reporter plasmid containing three tandem repeats of the M6-1892S sites was made and named pGLP-VF471×3.

Figure 4:
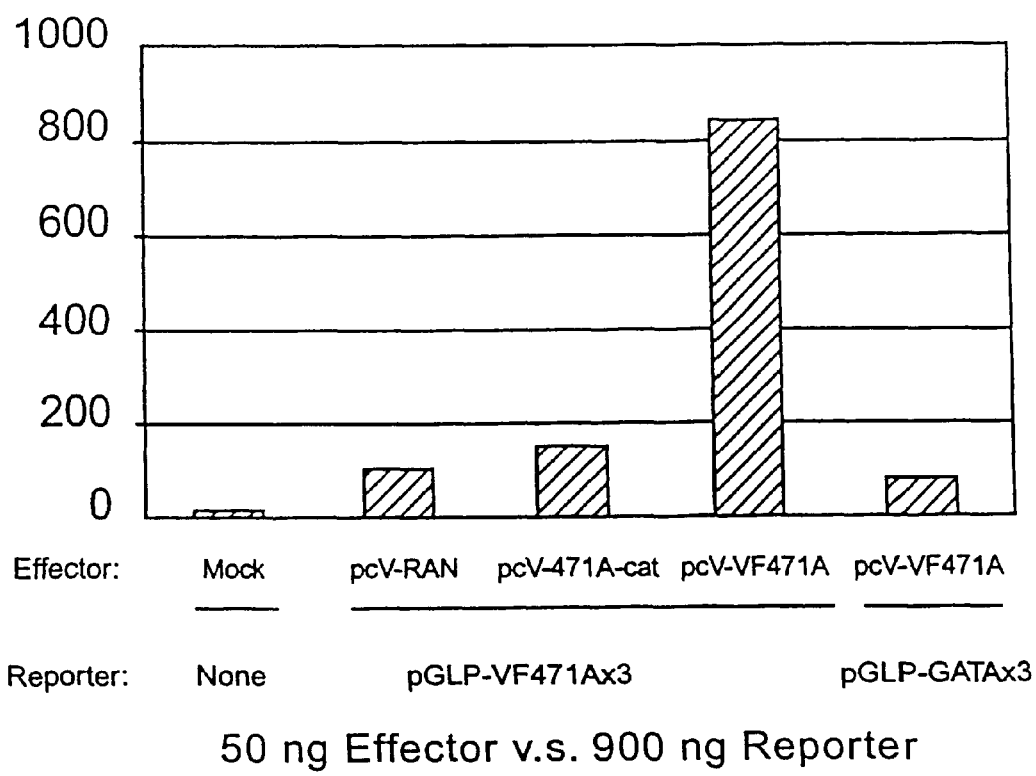
FIG. 4 shows the effect of zinc finger proteins on luciferase reporter gene activation.

All plasmid DNA was prepared using Qiagen plasmid purification kits. The human embryonic kidney 293 cells were seeded into each well of a 6-well plate with a density to reach approximately 70% confluence the next day. Cells were co-transfected with 50 ng effector DNA (ZFP-expression plasmid), 900 ng reporter DNA and 100 ng pCMV-LacZ DNA using either Lipofectamine (GIBCO-BRL., MD) or GenePORTER (Gene Therapy Systems Inc, CA) transfection reagent. The co-expressed β-galactosidase activity was used a control to normalize the luciferase activity. Cell lysates were harvested 40 to 48 hours after transfection. Luciferase assays were performed using the Dual-Light Luciferase and β-galactosidase Reporter Assay System (Tropix, MA). A typical luciferase assay result is shown in FIG. 4.

This example demonstrated that this designed ZFP-expressing plasmid, pcV-VF471A, was able to stimulate the luciferase gene expression by 8 fold when compared with control plasmid pcV-RAN, which does not possess known DNA binding capability. When the VP16 domain was replaced with a peptide, which has no transcription regulation activity, this zinc finger protein (pcV-VF471A-cat) lost its activity of trans-activating the luciferase gene. The designed zinc finger protein (pcV-VF471A) failed to activate the luciferase expression from the reporter containing a different zinc finger protein binding site, indicating that the trans-activation effect is sequence specific. Therefore, the DNA binding domain (VF471A ZFP) combined with the regulation domain (VP16) in this example were able to turn on the gene at an appropriate target sites.

Testing a Reporter Containing Native Promoter of the Targeted Gene in Transiently Transfected Cells The difference between the simple reporter system and the native reporter system is that the native reporter plasmid construct contains the promoter of the targeted gene. A unique advantage for the native reporter system is that a single native reporter plasmid construct can be used to analyze the effects of multiple zinc finger proteins in the context of the promoter.

The pGLP-native reporter was constructed by replacing the SV40 promoter in pGL3-promoter with a DNA fragment containing the promoter and flanking sequences of the targeted gene (FIG. 3). In this example, the native reporter construct of the human VEGF gene was generated by PCR-amplifying a 3319-bp fragment from the human genomic DNA. This fragment contains the VEGF promoter and its flanking regions. The VEGF ATG codon was fused to the luciferase coding region. Nest-PCR is performed for the amplification. The external primers were hVEGFU1 (5'-GAATTCTGTGCCCTCACTCCCTG (SEQ ID NO:16); nt 1 to 25 based on GenBank sequence M63971) and VEGFD2 (5'-ACCGCTTACCTTGGCATGGTGGAGG (SEQ ID NO:17); nt 3475 to 3451). The internal primer pair are hVEBFU2 (5'-ACACACCTTGCTG GGTACCACCATG (SEQ ID NO:18); nt 71 to 95, KpnI site underlined)) and VEGFD1 (5'-GCAGAAAGT cCATGGTTTCGGAGGCC (SEQ ID NO:19); nt 3413 to 3388, a T to C substitution is made to generate the underlined NcoI site). The nested PCR product was digested with KpnI and NcoI and ligated with the KpnI-NcoI vector fragment of the pGL3-promoter plasmid (FIG. 3). The human VEGF native reporter plasmid was named pGLPVFH.

A similar strategy was used to amplify a 2070-bp fragment from the mouse genomic DNA. The external primers were mVEGFU2 (5'-TGTTTAGAAGATGAACCGTAAGCCT (SEQ ID NO:20); nt 1 to 25 based on GenBank sequence U41383) and VEGFD2 (5'-ACCGCTTACCTTGGCATGGTGGAGG (SEQ ID NO:21); nt 3475 to 3451 based on M63971). The internal primers were mVEGF (5'-GCCCCCATT GGtACCCTGGCTTCAGTTCCCTGGCAACA (SEQ ID NO:22); nt 155 to 192; a C to T replacement is made to generate the underlined KpnI site) and VEGFD (5'-GCAGAAAGTcCATGGTTTCGGAGGCC (SEQ ID NO:23); nt 3413 to 3388 based on M63971; a T to C substitution is made to generate the underlined NcoI site). VEGFD2 and VEGFD1 primers were used to amplify both human and mouse genomic DNA since the sequences are highly homologous at that region (Shima et al. *J. Biol. Chem.* 271:3877 (1996)). The murine VEGF native reporter plasmid was called pGLPmVF.

Figure 5:
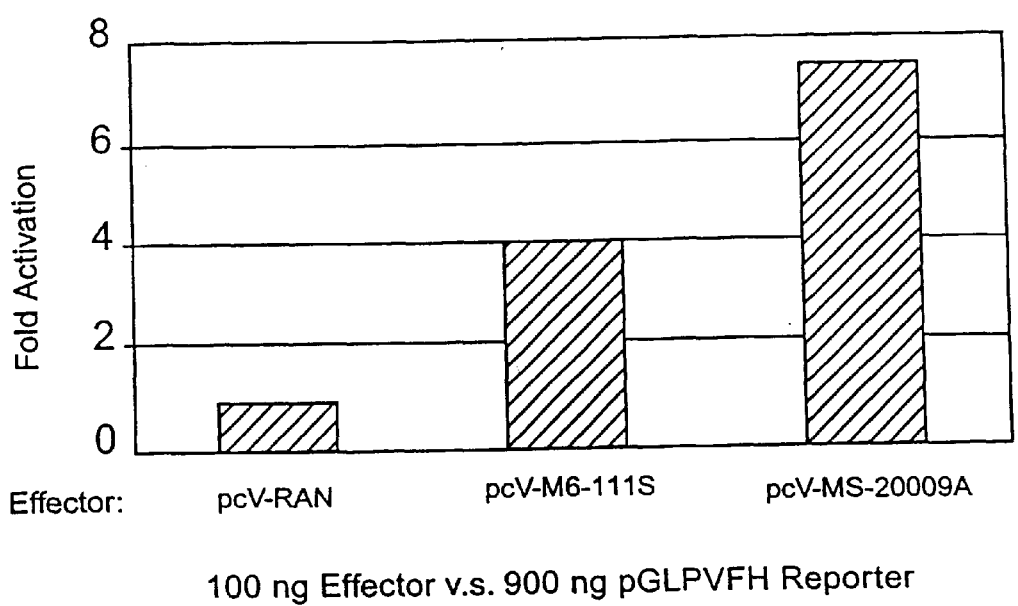
FIG. 5 shows activation of a human VEGF native reporter gene by zinc finger proteins.

The following example demonstrates that two designed zinc finger proteins were able to up-regulate the human VEGF native promoter gene in 293 cells. One zinc finger protein (pcV-M6-2009A) was designed to target a proximal site GAAGGGGGC located at 362-bp upstream of the transcription start site and the other one (pcV-M6- 11 S) was designed to target a distal site ATGGGGGTG located at 2240-nt upstream of the transcription start site. Similar to the luciferase reporter assay described above, 50 to 100 ng of effector DNA are co-transfected with 900 ng of native reporter DNA and 100 ng of pCMVlacZ DNA. Luciferase activities were measured approximately 40 hours post-transfection and were shown as fold activation in FIG. 5.

Primary Zinc Finger Proteins to Activate or Repress the Endogenous Human and Mouse VEGF Genes in Cell Culture To test whether these engineered zinc finger proteins can activate or repress the endogenous human and mouse VEGF genes in cell culture, transient transfection experiments were conducted. The human 293 cells and mouse mammary epithelial cells C1271 (Shima et al., *JBC* 271:3877 (1996)) express low levels of endogenous VEGF proteins, which are used to evaluate the zinc finger protein effect on VEGF activation. The human glioblastoma U87MG cells, the mouse neuroblastoma NB41 cells (Levy et al., *Growth Factors* 2:9 (1989)) and the rat glioma GS-9L cells (Conn et al., *Proc. Natl. Acad. Sci. U.S.A.* 87:1323 (1990)) express high levels of endogenous VEGF proteins, which are used for testing the repression effects of the zinc finger proteins. These cells are seeded into each well of a 6-well plate with a density to reach approximately 70% confluence the next day. 0.1 to 1 g effector DNA are usually used to transfect the cells using either Lipofectamine or GenePORTER transfection reagent depends on the cell types. Approximately 14 hours after transfection, cells are fed with fresh medium and cultured for another 24 hours. The mediums are then harvested and endogenous VEGF levels are measured using the VEGF ELISA Assay kits (R&D Systems, MN).

The VEGF M6-111S and M6-2009S ZFPs were designed as primary zinc finger proteins to test their activities in human VEGF gene regulation. The results in Table 1 indicated that both primary zinc finger proteins significantly activated the human endogenous VEGF gene expression in 293 cells.

Secondary Zinc Finger Proteins to Activate or Repress the Endogenous Human and Mouse VEGF Genes in Cell Culture To confirm that the physiological effects observed using the primary zinc finger proteins are due to the effects on the VEGF gene and not other side effects such as regulation of alternative gene targets, secondary zinc finger proteins that target the VEGF gene at sites different than that of the primary zinc finger protein were engineered. As shown in Table 1, the two secondary zinc finger proteins also activate the endogenous VEGF gene expression in cultured cells. These results demonstrated that the zinc finger protein technology can be used to regulate gene expression and to validate a gene as a target for therapeutics.

Tertiary Zinc Finger Proteins to Target the Genes Not Involved in VEGF Physiology To confirm that the physiological effects observed using the primary and secondary zinc finger proteins are due to the specific effects on the VEGF gene and not any non-specific DNA-binding or squelching effects, tertiary zinc finger proteins that target genes not involved in VEGF physiology are used as negative controls. For example, a zinc finger protein designed for regulating human EPO gene expression is used as a specificity control (see Example II). EPO is also affected by hypoxia and thus is useful as a control for VEGF target validation using a hypoxia assay. VEGF inhibition specifically reverses diabetic retinopathy. This result validates VEGF as a molecular target for drug discovery and development.

Test the VEGF Inhibition Effect on a Diabetic Retinopathy Model in Rodents

Diabetic retinopathy is the most common cause of blindness amongst individuals of working age. Increased VEGF expression is a major contributor for the pathology of diabetic retinopathy. One of the strategies to treat this disease is to inhibit endogenous VEGF gene expression using therapeutic compounds. As described above, zinc finger proteins provide the means to validate VEGF as a therapeutic target. Adeno-associate virus (AAV) and or retrovirus-based viral vectors are constructed as described

TABLE 1

Activation of Human Endogenous VEGF Gene by zinc finger proteins in 293 Cells

|  | Effector | Target | Location* | Reporter | Fold Activation |
| --- | --- | --- | --- | --- | --- |
| Vector control | pcV-RAN | None | N/F | pGLPVFH | 1 |
| Primary ZFP | pcV-M6-111S | ATGGGGGTC | −2252 | pGLPVFH | 4.1 |
| Primary ZFP | pcV-M6-2009S | GAAGGGGGC | −363 | pGLPVFH | 4.5 |
| Secondary ZFP | pcV-M6-120S | GGGGGTGCC | −2243 | pGLPVFH | 13.8 |
| Secondary ZFP | pcV-M6-1878S | GAGTGTGTG | −536 | pGLPVFH | 4.2 |

*Distance between the target sites and the VEGF transcription initiation site.
N/F: Not found in the vicinity of the VEGF promoter region.

To repress the targeted gene, the designed zinc finger protein domains were cloned into the pcDNA-NKF vector. After transfection of the DNA into the appropriate cells, the ZFP-KRAB fusion proteins can inhibit the endogenous gene as well as the cotransfected luciferase reporter gene. The example used here is pcK-M6-11S. As shown in Table 1, M6-111S ZFP recognizes the target sequence ATGGGGGTG. When the M6-111S ZFP fused to KRAB repression domain, an approximately 80% repression on the cotransfected luciferase reporter gene expression and approximately 40% repression on the endogenous VEGF gene expression were achieved.

above. These virus vectors express the zinc finger proteins that are fused with the KRAB repression domain as described above. The viruses are generated, purified, and injected into the animals. The efficacy of the engineered zinc finger proteins is evaluated by suppression of retinal neovascularization as previously described (Admais et al., *Arch. Ophthalmol.* 114:66 (1996); Pierce et al, *Proc. Natl. Acad. Sci. U.S.A.* 92:905 (1995); Aiello et al., *Proc. Natl. Acad. Sci. U.S.A.* 92:10457 (1995); Smith et al., *Invest. Ophthalmol. Vis. Sci.* 35:101, 1994). All necessary controls, including the viral vectors expressing the secondary and tertiary zinc finger proteins are also used.

Test the VEGF Activation Effect on a Peripheral Artery Disease Model in Rodents

Stimulation of peripheral angiogenesis by VEGF to augment collateral artery development is a potentially novel form of therapy for patients with ischemic vascular disease. The same strategy described above is used to validate VEGF as a target using a mouse peripheral artery disease model. The AAV or retrovirus vectors, which express the zinc finger proteins fused to VP16 activation domain, are constructed as described above. The efficacy of the zinc finger proteins are evaluated similar to the procedures described previously (Couffinhal et al., *Am. J. Pathol.* 152:1667 (1998); Takeshita et al., *Lab. Invst.* 75:487 (1996); Isner et al., *Human Gene Therapy* 7:959(1996)). All necessary controls, including the viral vectors expressing the secondary and tertiary zinc finger proteins are also used. VEGF overexpression triggers collateral artery growth. This result validates VEGF as a target for drug discovery and development.

Example II

Erythropoiesis Target Discovery

Mammalian erythropoiesis is regulated via stimulation of the erythroid progenitors by certain factor(s) that provide proliferation and differentiation signals. Hypoxia is a potent signal that induces the expression of genes controlling many physiologically relevant processes (Ratcliffe et al. *J. Exp. Biol.* 201:1153 (1998)). One of the processes is to "request" that certain tissues release a factor(s) for the production of additional red blood cells. This phenomenon can be detected by stimulating different cell lines and/or tissues with hypoxic conditions, sampling the culture supernatants, and testing for the stimulation of erythrocyte colony forming units from murine bone marrow cultures. Cell lines or tissues found to respond to hypoxia in this way likely express erythropoietic growth factors in a hypoxia inducible manner. The analysis of genes differentially expressed in such cells or tissues upon hypoxic treatment should lead to the identification of erythropoietic growth factor expressing genes. Zinc finger protein technology can be used as analytical tools for such differential gene expression experiments and to validate the hypothetical erythropoietic growth factor genes.

A collection of cell types (including human hepatoma cell line, Hep3B) are cultured in appropriate medium and maintained in a humidified 5% $CO_2$-95% air incubator at 37° C. Hypoxic conditions are achieved by flushing 1% $O_2$-5% $CO_2$-94% $N_2$ for 18 hours (Goldberg et al., *Blood* 77:271 (1991)). The culture supernatants are harvested and tested in colony forming assay (Muller et al., *Exp. Hematol.* 21:1353 (1993); Eaves & Eaves, *Blood* 52:1196 (1978)). The human hepatoma Hep3B cell line is found to produce an erythropoietic growth factor(s) upon hypoxic induction (Goldberg et al. *Proc. Natl. Acad. Sci. U.S.A.* 84:7972 (1987)) and this cell line is used for further characterization.

One working hypothesis is that one (or more) of the cellular genes, which are responsible for stimulating red cell production, is activated upon hypoxia. This gene(s) may be identified by performing a differential gene expression experiment, such as Differential Display (GeneHunter, TN), PCR-Select cDNA Subtraction (Clontech, CA), or microarray (Affymetrix, CA). The gene expression patterns of the RNA extracted from the Hep3B cells growing under normal and hypoxic conditions are compared.

It is very likely that multiple genes are up-regulated in the hypoxic cells. Approximately eighteen genes have been identified as up-regulated by hypoxia (Ratcliffe et al,. *J. Exp. Biol.* 201:1153 (1998)). The erythropoietin (EPO) gene and the vascular endothelial growth factor (VEGF) gene, which have been extensively studied, are used in this example to demonstrate the application of the zinc finger protein technology to functional genomics and identification of the gene encoding the erythropoietic growth factor.

Based on the DNA sequences of the candidate genes identified from the above experiments, primary zinc finger protein s are designed to target the DNA sequences located in a proximity of the promoters. The zinc finger protein construction and characterization process is the same as that described in the Example I. The zinc finger proteins (a 3-finger one or a 6-finger protein) with high DNA-binding affinity and specificity are fused with either the HSV VP-16 activation domains or the KRAB repression domains to activate or block expression of the individual genes on the list.

These designed ZFP-VP16 constructs are individually transiently transfected into Hep3B cells using the GenePORTER transfection reagent (Gene Therapy Systems Inc, CA) under the non-hypoxic condition. 48 hours post-transfection, the supernatants are collected and the colony forming assays are performed. The gene(s) that induces the red cell production upon zinc finger protein up-regulation is considered to be the gene(s) that encodes an erythropoietic growth factor. The results indicate that the erythropoietin (EPO) gene is responsible for the erythropoiesis regulation while all other tested genes (including VEGF) are not. All necessary zinc finger protein control constructs described in Example I are also used in this example.

Another way to identify and validate the gene is to perform the similar experiments described above except that these zinc finger proteins are fused with the KRAB domains and the Hep3B cells are stimulated by hypoxia 14 hours post-transfection. When the zinc finger proteins, which are designed to repress the EPO gene expression, are transfected into the Hep3B cells, no or reduced activity based on the colony forming assay is observed. All zinc finger proteins, which target genes other than the EPO gene, do not affect the red cell production under hypoxic induction.

To further validate the gene function, secondary zinc finger proteins, which target at different sites of the EPO gene, are constructed. These secondary zinc finger proteins, when fused with VP16 activation domains, activate the EPO gene expression and stimulate the red cell production. Conversely, when fused with KRAB repression domains, these zinc finger proteins inhibit the EPO gene expression under hypoxic condition and fail to stimulate the red cell production.

Example III

Breast Cancer Target Gene Discovery

The growth of some breast tumors depends on the continued presence of the hormone estrogen. Estrogen is likely involved in the up-regulation of genes required for maintenance of the transformed phenotype. Cell lines derived from these tissues (such as MCF-7, BT20 and T47D) retain this dependence on estrogen for growth in culture. Thus, it appears estrogen stimulates expression of essential genes in the dependent cell lines. The discovery of these estrogen-induced genes are useful molecular targets for the development of new drugs to treat breast cancer. The use of zinc finger proteins to identify estrogen-induced genes required for estrogen-dependent cell growth is described herein.

Furthermore, the newly discovered targets are validated using zinc finger proteins and appropriate controls.

Identifying ER-responsive Genes

MCF-7 cells are grown in the absence of estrogen (estradiol) for short term (1 week) and long term (28 weeks) to allow transcription of estradiol-induced genes to reach basal levels. Cells are propagated in 162 ml flasks, containing Dulbecco's Modified Eagle Medium (DMEM), lacking phenol red and supplemented with 10% charcoal-stripped Fetal Calf Serum (FCS) (Hyclone), 10 µg/ml insulin and 0.5 nM estradiol. Upon reaching 80% confluency, cells will trypsinized and transferred to fresh medium lacking estradiol. The flasks are incubated at 37° C. in a humidified atmosphere of 5% $CO_2$.

Estrogen-responsive gene expression is stimulated by adding estradiol to the cells. The cells grown in the absence of estradiol are split into fresh medium lacking estradiol. One flask will receive 10 nM estradiol (dissolved in ethanol) while the other will receive an equivalent amount of ethanol not containing estradiol. Both stimulated and unstimulated cells are harvested after 6 hrs.

RNA is isolated from the cells for identifying differentially expressed genes using a standard RNA isolation kit. Estrogen responsive genes are identified using one or a combination of the following methods; subtractive hybridization such as PCR-Select from Clontech, differential display methods such as the READS technology offered by Genelogic, or Perkin-Elmer's GenScope, cDNA arrays such as GEM technology from Incyte, or a high-density oligonucleotide matrix technologies offered by Affymetrix.

A number of differentially expressed (estradiol activated) genes should be identified. The cDNAs for these genes are sequenced and compiled into a list of candidate genes. It is expected that many genes will be identified, including the estrogen receptor.

Initial Validation of Estrogen-responsive Genes

Zinc finger proteins are engineered to target each of the individual members of the list of candidate genes, as described above and in co-pending application U.S. Ser. No. 09/229,037. The sequences of candidate genes are scanned for unique and easily targetable 9 bp sequences. This process will include searching databases for matches to previously sequenced genes in order to obtain additional sequences and to confirm the accuracy of the cDNA sequence generated above.

These designed zinc finger proteins are fused to functional domains, allowing both up regulation and knock-down of expression of the candidate genes, as described above. The functional domains to be employed are the Kruppel-associated box (KRAB) repression domain and the herpes simplex virus (HSV-1) VP16 activation domain.

Repression of Candidate Genes

For repressor studies, cells harboring the individual zinc finger proteins are assayed for failure to grow due to blocking estrogen-dependent functions. It has been established that estrogen receptor is essential for growth in MCF-7; hence these cells should fail to grow when the ER gene or other estrogen dependent functions are targeted for down regulation.

Cells are cultured in the medium previously described with and without estradiol. Eukaryotic expression vectors, constructed to fuse the zinc finger proteins to the SV40 NLS and KRAB, are described above. Transfections are done using Lipofectamine, a commercially available liposome preparation from GIBCO-BRL. All plasmid DNAs are prepared using Qiagen Midi DNA purification system. 10 g of the effector plasmid is mixed with 100 ng Lipofectamine (50 µl) in a total volume of 1600 µl of Opti-MEM. A pCMV β-gal plasmid (Promega) will also be included in the DNA mixture as an internal control for transfection efficiency. Following a 30 minute incubation, 6.4 ml of DMEM is added and the mixture was layered on the cells. After five hours, the DNA-Lipofectamine mixture is removed, and fresh culture medium containing 10% charcoal-stripped FCS, 10 µg/ml insulin and 10 nM estradiol are layered on the cells.

Viability is assayed by trypan blue exclusion and monitoring growth. Cells are trypsinized, concentrated by centrifugation and resuspended at approximately $10^6$ cells/ml. A solution of 0.4% trypan blue is added to an equal volume of cells on a hemocytometer slide. Total and stained cells are counted under a microscope. Growth is monitored by measuring DNA synthesis. Radioactive [$^3$H]thymidine (0.5 µCi at 30 Ci/mmol; Ammersham) is added and the cells are allowed to grow for an additional 17 h. The medium is removed and cells are lysed in situ with 1% SDS. Cell lysates are precipitated with 15% trichloroacetic acid (TCA) and collected by filtration with Whatman 3M filter discs and washed with 5% TCA then ethanol. Filters are dried and thymidine incorporation is quantitated by liquid scintillation counting.

Activation of Candidate Genes

Activation of each member of the list will also be performed to assay for estrogen-independent growth of MCF-7 cells. Eukaryotic expression vectors are constructed as described above. Transfections are done using Lipofectamine, a commercially available liposome preparation from GIBCO-BRL. All plasmid DNAs are prepared using the Qiagen Midi DNA purification system. Transfection is performed as described above Viability is assayed by trypan blue exclusion and monitoring growth. Cells are trypsinized, concentrated by centrifugation and resuspended at approximately $10^6$ cells/ml. A solution of 0.4% trypan blue is added to an equal volume of cells on a hemocytometer slide. Total and stained cells are counted under a microscope. Growth is monitored by measuring DNA synthesis. Radioactive [$^3$H]thymidine (0.5 µCi at 30 Ci/mmol; Ammersham) is added and the cells are allowed to grow for an additional 17 h. The medium is removed and cells are lysed in situ with 1% SDS. Cell lysates are precipitated with 15% trichloroacetic acid (TCA) and collected by filtration with Whatman 3M filter discs and washed with 5% TCA then ethanol. Filters are dried and thymidine incorporation is quantitated by liquid scintillation counting.

Secondary Validation

Additional testing will validate candidate genes identified during this first round of repressor and activator studies. These zinc finger proteins are designed to target two distinct and separated target sites in the candidate gene. Additionally, the specificity and affinity of the zinc finger proteins are improved by fusing two three finger zinc finger protein domains to form a six finger molecule that recognizes 18 bp.

Three finger zinc finger proteins are designed, produced and assayed by EMSA as described herein. In order to locate suitable sequences, for which zinc finger proteins can be easily and reliably designed, additional sequencing of the candidate genes may be required. Furthermore, additional sequences may be found in nucleotide sequence databases. Target sequences are chosen so that two 9 bp sequences are within 5 bp of each other; thus allowing linking of the zinc finger protein pairs. After identifying pairs of three finger zinc finger proteins that bind with acceptable affinities and specificities, the domains are linked by PCR, amplifying the domain which constitutes fingers 4–6 of the six finger molecule. A short DNA sequence encoding a peptide sequence predicted to be unstructured and flexible is added to the N-terminus of this domain during amplification.

Each construct is transiently transfected into MCF-7 cells growing in culture and is scored for failure to grow (repression) or estrogen-independent growth (activation) as described above.

Target Validation Using Xenografts

The effects of altered target gene expression on tumor growth is assessed by xenografts in nude mice. The genes encoding the zinc finger proteins are cloned into adeno-associated virus (AAV) or retrovirus-based viral vectors as described above. The zinc finger proteins are fused to either KRAB or VP16 domains. The resulting recombinant viruses are generated, purified and used to infect MCF-7 cells. These transgenic cells are introduced subcutaneously into nude mice (Bissery et al., *Semin. Oncol.* 22:3–16 (1995)). Tumors are measured twice weekly in order to estimate tumor weight (Bissery et al., *Semin. Oncol.* 22:3–16 (1995); Kubota et al., *J. Surg. Oncol.* 64:115–121 (1997)). The experiment is allowed to progress until tumors obtain a weight of 100–300 mg or the animals die.

End-point assays will include macroscopic examination of the thoracic and abdominal cavities to determine probable cause of death. Additional assays will include histological analysis of tissue samples and excision of tumors for weighing.

Example IV

Fatty Acid Saturation Target Discovery in Plants

Vegetable oil quality is determined in part by the degree of saturation of the component fatty acid side chains. Excessive desaturation (beyond one or two double bonds) leads to poorer quality oils that are more prone to oxidation and rancidity. Components of the biosynthetic machinery in oil producing seeds determine the degree of desaturation. Inhibiting the expression of a gene whose product is involved in fatty acid desaturation may lead to higher quality oils. Zinc finger proteins are used as probes for differential gene expression experiment in order to identify genes that play a role in setting the level of fatty acid saturation. Primary, secondary and tertiary zinc finger proteins are used to validate the newly discovered gene function. Finally, transgenic plants, producing higher quality oils, are produced.

Generating Candidate Genes Through Random Mutagenesis

Starting material is either soybean (Glycine max) seeds or plants. Mutagenesis is performed by either chemical treatment or random DNA insertion (Katavic et al., *Plant. Physiol.* 108:399–409 (1995); Martienssen, *Proc. Natl. Acad. Sci. U.S.A.* 95:2021–2026 (1998); Hohn & Puchta, *Proc. Natl. Acad. Sci. U.S.A.* 96:8321–8323 (1999); Facciotti et al., *Nature Biotech.* 17:593–597 (1999)).

Chemical mutagenesis of seeds is performed by soaking in 0.3% (v/v) ethylmethanesulfonate (EMS) for 16 h (Haughn & Somerville, *Mol. Gen. Genet.* 204:430–434 (1986)). $M_1$ seeds are propagated and allowed to self-fertilize, then $M_2$ seeds are randomly collected and propagated followed by another round of self-fertilization to form $M_3$ seeds. The fatty acid composition of the seeds and resulting plants is analyzed as described below.

Alternatively, random DNA insertion can be performed by transposition using a number of systems developed in plants (Martienssen, *Proc. Natl. Acad. Sci. U.S.A.* 95:2021–2026 (1998)).

Identifying Potential Candidate Genes by Fatty Acid and Lipid Analyses

Fatty acid and lipid composition is determined for approximately 20–30 of the $M_3$ seeds according to the method of Katavic (*Plant Physiol.* 108:399–409 (1995)). Mature plant tissues are also similarly analyzed. Seeds are grouped into categories according to degree of fatty acid saturation.

Expression profiles are generated for seeds expressing either elevated or reduced degrees of desaturation by employing one of the methods described in Example III. (Note: FAD2-1, encoding omega-6-desaturase, is expected to be a gene underexpressed in seeds that will lower levels of polyunsaturated long chain fatty acids). Once a particular gene has been identified as participating in the altered phenotype, the cDNA is selected for sequencing.

Initial Target Validation with Primary Zinc Finger Proteins

Zinc finger proteins are engineered to target each of the individual members of the list of candidate genes, as described above and in co-pending application U.S. Ser. No. 09/229,037. The sequences of candidate genes are scanned for unique and easily targetable 9 bp sequences. This process includes searching databases for matches to previously sequenced genes in order to obtain additional sequences and to confirm the accuracy of the cDNA sequence generated above.

These designed zinc finger proteins are fused to functional domains, allowing both up regulation and knock-down of expression of the candidate genes, as described above. The functional domains to be employed are the Kruppel-associated box (KRAB) repression domain and the herpes simplex virus (HSV-1) VP16 activation domain.

The genes encoding the ZFP-functional domain fusions are cloned into a plant expression vector such as pCAM-BIA1301. This vector possesses the following attributes: 1) a selectable marker such as the gene encoding hygromycin resistance; 2) left and right T-DNA borders for Agrobacterium-mediated transformation; 3) convenient restriction sites which will allow insertion of the zinc finger protein gene downstream of desired promoters (such as CaMV 35S, napin or phaseolin promoters); 4) a plant polyadenylation signal such as Nos; 5) a GUS reporter gene.

Designed zinc finger proteins are tested for activity against the desired target by assaying activation or repression of reporter genes. A single plasmid that independently expresses the zinc finger protein and the reporter is used. The target sequence is inserted in the DNA near the start site for transcription for the GUS gene. Transformation of reporter constructs into tobacco callus is carried out by standard co-cultivation procedures (Grayburn et al., *Biotechnol.* 10:675–678 (1992)). GUS assays are conducted using a fluorometric assay (Jefferson, *Plant Mol. Bio. Rep.* 5:387–405 (1987)).

Zinc finger proteins that demonstrate acceptable affinities as assessed by EMSA and in vivo function as assessed by reporter assays are transformed into soybean somatic embryos via particle bombardment of proliferating embryogenic cultures derived from cotyledons of immature seeds (Liu et al., *Plant Cell Tiss. Org. Cult.* 46:33–42 (1996)).

Tissues and seeds derived from 10–20 separate transformation events for each ZFP-bearing plasmid are isolated to assess fatty acid and lipid profiles. Candidate genes which produce an altered fatty acid or lipid profile when transformed with the above zinc finger proteins are selected for secondary and tertiary designs which will generate more specific zinc finger proteins.

Secondary and Tertiary Zinc Finger Proteins to Further Validate Target in Desaturation Pathway Additional testing is used to validate candidate genes identified during this first round of repressor and activator studies. These zinc finger proteins are designed to target two distinct and separated target sites in the candidate gene. Additionally, the specificity and affinity of the zinc finger proteins are improved by fusing two three finger zinc finger protein domains to form a six finger molecule that recognizes 18 bp.

Three finger zinc finger proteins are designed, produced and assayed by EMSA as described herein. In order to locate suitable sequences, for which zinc finger proteins can be easily and reliably designed, additional sequencing of the candidate genes may be required. Furthermore, additional sequences may be found in nucleotide sequence databases. Target sequences are chosen so that two 9 bp sequences are within 5 bp of each other; thus allowing linking of the zinc finger protein pairs. After identifying pairs of three finger zinc finger proteins that bind with acceptable affinities and specificities, the domains are linked by PCR, amplifying the domain which constitutes fingers 4–6 of the six finger molecule. A short DNA sequence encoding a peptide sequence predicted to be unstructured and flexible is added to the N-terminus of this domain during amplification.

Six finger zinc finger proteins are fused to either repression or activation domains and assayed first in tobacco callus reporter studies then in soybean plants as described herein.

Candidate genes that produce altered fatty acid or lipid profiles when targeted by the secondary zinc finger proteins described above are selected for design of tertiary zinc finger proteins. A second region of the gene separate from that targeted with the secondary zinc finger proteins is chosen. Again, zinc finger proteins designed to bind 18 bp are designed and tested as described herein. These zinc finger proteins are introduced into soybean and the resulting alteration on fatty acid and lipid profiles will again be examined.

What is claimed is:

1. A method for establishing an association between a gene and a selected phenotype in a cell, the method comprising the steps of:
   (i) identifying a plurality of candidate genes, wherein at least one of the candidate genes is not operably linked to heterologous sequences;
   (ii) providing a first engineered zinc finger protein that binds to a first target site of a first candidate gene;
   (iii) culturing a first cell under conditions where the first zinc finger protein contacts the first candidate gene, wherein the first zinc finger protein modulates expression of the first candidate gene;
   (iv) determining the expression pattern of the candidate genes and determining whether or not the first candidate gene is associated with the selected phenotype; and;
   (v) repeating steps (ii)–(v) for each candidate gene.

2. The method of claim 1, further comprising providing a second zinc finger protein that binds to a second target site of the first candidate gene.

3. The method of claim 1, wherein at least one of the candidate genes is an EST of at least about 200 nucleotides in length.

4. The method of claim 1, wherein at least two candidate genes are required to cause the selected phenotype.

5. The method of claim 1, wherein the candidate genes are endogenous genes.

6. The method of claim 1, wherein expression of the candidate genes is inhibited by at least about 50%.

7. The method of claim 1, wherein expression of the candidate genes is activated to at least about 150%.

8. The method of claim 1, wherein the zinc finger proteins are fusion proteins comprising a regulatory domain.

9. The method of claim 8, wherein the regulatory domain is under small molecule control.

10. The method of claim 8, wherein the zinc finger proteins are fusion proteins comprising at least two regulatory domains.

11. The method of claim 8, wherein the regulatory domain is selected from the group consisting of a transcriptional repressor, a methyl transferase, a transcriptional activator, a histone acetyltransferase, and a histone deacetylase.

12. The method of claim 1, wherein the cell is selected from the group consisting of animal cell, a plant cell, a bacterial cell, a protozoal cell, or a fungal cell.

13. The method of claim 12, wherein the cell is a mammalian cell.

14. The method of claim 13, wherein the cell is a human cell.

15. The method of claim 1, wherein the modulation of expression of a candidate gene is activation of gene expression that prevents repression of gene expression.

16. The method of claim 1, wherein the modulation of expression of a candidate gene is inhibition of gene expression that prevents gene activation.

17. The method of claim 1, wherein the zinc finger protein is encoded by an expression vector comprising a zinc finger protein nucleic acid operably linked to a promoter, and wherein the method further comprises the step of first administering the expression vector to the cell.

18. The method of claim 17, wherein expression of the zinc finger protein is under small molecule control.

19. The method of claim 17, wherein the expression vector is a viral vector.

20. The method of claim 19, wherein the expression vector is a retroviral expression vector, an adenoviral expression vector, or an AAV expression vector.

21. The method of claim 17, wherein the zinc finger protein is encoded by a nucleic acid operably linked to an inducible promoter.

22. The method of claim 1, wherein the cell comprises less than about $1.5 \times 10^6$ copies of the zinc finger protein.

23. The method of claim 1, wherein the target site is upstream of a transcription initiation site of the candidate gene.

24. The method of claim 1, wherein the target site is adjacent to a transcription initiation site of the candidate gene.

25. The method of claim 1, wherein the target site is adjacent to an RNA polymerase pause site, wherein the RNA polymerase pause site is downstream of a transcription initiation site of the candidate gene.

26. A method for establishing an association between a gene and a selected phenotype in a cell, the method comprising the steps of:
   (i) selecting a first candidate gene, wherein the first candidate gene is not operably linked to heterologous sequences;
   (ii) providing a first engineered zinc finger protein that binds to a target site of the first candidate gene and second zinc finger protein that binds to a second target site of the first candidate gene;
   (iii) culturing a first cell under conditions where the first zinc finger protein contacts the first candidate gene, and culturing a second cell under conditions where the second zinc finger protein contacts the first candidate gene, wherein the first and the second zinc finger proteins modulate expression of the first candidate gene; and
   (iv) assaying the first and second cells for a selected phenotype, thereby identifying whether or not the first candidate gene is associated with the selected phenotype.

27. The method of claim 26, further comprising providing a third zinc finger protein that binds to a target site of a second gene.

28. The method of claim 27, wherein the first candidate gene and the second gene are both required for causing the selected phenotype.

29. The method of claim 26, further comprising selecting a plurality of candidate genes and providing a plurality of zinc finger proteins that bind to a target site of each candidate gene.

30. The method of claim 26, wherein the first candidate gene is an EST of at least about 200 nucleotides in length.

31. The method of claim 26, wherein the first and second cell are the same cell.

32. The method of claim 26, wherein the first candidate gene is an endogenous gene.

33. The method of claim 26, wherein expression of the first candidate gene is inhibited by at least about 50%.

34. The method of claim 26, wherein expression of the first candidate gene is activated to at least about 150%.

35. The method of claim 26, wherein the zinc finger proteins are fusion proteins comprising a regulatory domain.

36. The method of claim 35, wherein the regulatory domain is under small molecule control.

37. The method of claim 35, wherein the zinc finger proteins are fusion proteins comprising at least two regulatory domains.

38. The method of claim 35, wherein the regulatory domain is selected from the group consisting of a transcriptional repressor, a methyl transferase, a transcriptional activator, a histone acetyltransferase, and a histone deacetylase.

39. The method of claim 26, wherein the cell is selected from the group consisting of animal cell, a plant cell, a bacterial cell, a protozoal cell, or a fungal cell.

40. The method of claim 39, wherein the cell is a mammalian cell.

41. The method of claim 40, wherein the cell is a human cell.

42. The method of claim 26, wherein the modulation of expression is activation of gene expression that prevents repression of gene expression.

43. The method of claim 26, wherein the modulation of expression is inhibition of gene expression that prevents gene activation.

44. The method of claim 26, wherein the first and the second zinc finger proteins are encoded by expression vectors comprising a zinc finger protein nucleic acid operably linked to a promoter, and wherein the method further comprises the step of first administering the expression vectors to the cells.

45. The method of claim 44, wherein expression of the zinc finger proteins is under small molecule control.

46. The method of claim 45, wherein expression of the first zinc finger protein and expression of the second zinc finger protein are under different small molecule control, wherein both the first and the second zinc finger protein are fusion proteins comprising a regulatory domain, and wherein the first and the second zinc finger proteins are expressed in the same cell.

47. The method of claim 46, wherein the first zinc finger protein comprises a regulatory domain that represses gene expression and the second zinc finger protein comprises a regulatory domain that activates gene expression.

48. The method of claim 44, wherein the expression vector is a viral vector.

49. The method of claim 48, wherein the expression vector is a retroviral expression vector, an adenoviral expression vector, or an AAV expression vector.

50. The method of claim 44, wherein the zinc finger proteins are encoded by a nucleic acid operably linked to an inducible promoter.

51. The method of claim 26, wherein the cell comprises less than about $1.5 \times 10^6$ copies of each zinc finger protein.

52. The method of claim 26, wherein the first or the second target site is upstream of a transcription initiation site of the first candidate gene.

53. The method of claim 26, wherein the first or the second target site is adjacent to a transcription initiation site of the first candidate gene.

54. The method of claim 26, wherein the first or the second target site is adjacent to an RNA polymerase pause site, wherein the RNA polymerase pause site is downstream of a transcription initiation site of the first candidate gene.

55. A method for establishing an association between a gene and a selected phenotype in a cell, the method comprising the steps of:
   (i) selecting a first candidate gene, wherein the first candidate gene is not operably linked to heterologous sequences;
   (ii) providing a first engineered zinc finger protein that binds to a first target site of the first candidate gene;
   (iii) culturing a first cell under conditions where the first zinc finger protein contacts the first candidate gene, wherein the first zinc finger protein modulates expression of the first candidate gene; and
   (iv) assaying for a selected phenotype, thereby identifying whether or not the first candidate gene is associated with the selected phenotype.

* * * * *

SEQUENCE LISTING

```
<160> NUMBER OF SEQ ID NOS:  23

<210> SEQ ID NO 1
<211> LENGTH: 25
<212> TYPE: PRT
<213> ORGANISM: Artificial Sequence
<220> FEATURE:
<223> OTHER INFORMATION: Description of Artificial Sequence:exemplary
      motif of C2H2 class of zinc finger proteins (ZFP)
<221> NAME/KEY: MOD_RES
<222> LOCATION: (2)..(3)
<223> OTHER INFORMATION: Xaa = any amino acid
<221> NAME/KEY: MOD_RES
<222> LOCATION: (4)..(5)
<223> OTHER INFORMATION: Xaa = any amino acid, may be present or absent
<221> NAME/KEY: MOD_RES
<222> LOCATION: (7)..(18)
<223> OTHER INFORMATION: Xaa = any amino acid
<221> NAME/KEY: MOD_RES
<222> LOCATION: (20)..(22)
<223> OTHER INFORMATION: Xaa = any amino acid
<221> NAME/KEY: MOD_RES
<222> LOCATION: (23)..(24)
<223> OTHER INFORMATION: Xaa = any amino acid, may be present or absent

<400> SEQUENCE: 1

Cys Xaa Xaa Xaa Xaa Cys Xaa Xaa Xaa Xaa Xaa Xaa Xaa Xaa Xaa Xaa
 1               5                  10                  15

Xaa Xaa His Xaa Xaa Xaa Xaa Xaa His
            20                  25

<210> SEQ ID NO 2
<211> LENGTH: 10
<212> TYPE: DNA
<213> ORGANISM: Artificial Sequence
<220> FEATURE:
<223> OTHER INFORMATION: Description of Artificial Sequence:ZFP target
      site with two overlapping D-able subsites
<221> NAME/KEY: modified_base
<222> LOCATION: (1)..(2)
<223> OTHER INFORMATION: n = g, a, c or t
<221> NAME/KEY: modified_base
<222> LOCATION: (5)
<223> OTHER INFORMATION: n = g, a, c or t
<221> NAME/KEY: modified_base
<222> LOCATION: (8)
<223> OTHER INFORMATION: n = g, a, c or t
<221> NAME/KEY: modified_base
```

```
<222> LOCATION: (9)
<223> OTHER INFORMATION: n = a, c or t; if g, then position 10 cannot
      be g or t

<400> SEQUENCE: 2 nngkngknnn                                                              10

<210> SEQ ID NO 3
<211> LENGTH: 10
<212> TYPE: DNA
<213> ORGANISM: Artificial Sequence
<220> FEATURE:
<223> OTHER INFORMATION: Description of Artificial Sequence:ZFP target
      site with three overlapping D-able subsites
<221> NAME/KEY: modified_base
<222> LOCATION: (1)..(2)
<223> OTHER INFORMATION: n = g, a, c or t
<221> NAME/KEY: modified_base
<222> LOCATION: (5)
<223> OTHER INFORMATION: n = g, a, c or t
<221> NAME/KEY: modified_base
<222> LOCATION: (8)
<223> OTHER INFORMATION: n = g, a, c or t

<400> SEQUENCE: 3 nngkngkngk                                                              10

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence:linker

<400> SEQUENCE: 4

Asp Gly Gly Gly Ser
 1               5

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence:linker

<400> SEQUENCE: 5

Thr Gly Glu Lys Pro
 1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence:linker

<400> SEQUENCE: 6

Leu Arg Gln Lys Asp Gly Glu Arg Pro
 1               5

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence:linker

<400> SEQUENCE: 7
```

```
Gly Gly Arg Arg
  1

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence:linker

<400> SEQUENCE: 8

Gly Gly Gly Gly Ser
  1               5

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence:linker

<400> SEQUENCE: 9

Gly Gly Arg Arg Gly Gly Gly Ser
  1               5

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence:linker

<400> SEQUENCE: 10

Leu Arg Gln Arg Asp Gly Glu Arg Pro
  1               5

<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence:linker

<400> SEQUENCE: 11

Leu Arg Gln Lys Asp Gly Gly Ser Glu Arg Pro
  1               5                  10

<210> SEQ ID NO 12
<211> LENGTH: 16
<212> TYPE: PRT
<213> ORGANISM: Artificial Sequence
<220> FEATURE:
<223> OTHER INFORMATION: Description of Artificial Sequence:linker

<400> SEQUENCE: 12

Leu Arg Gln Lys Asp Gly Gly Ser Gly Gly Ser Glu Arg Pro
  1               5                  10                  15

<210> SEQ ID NO 13
<211> LENGTH: 97
<212> TYPE: PRT
<213> ORGANISM: Artificial Sequence
<220> FEATURE:
<223> OTHER INFORMATION: Description of Artificial Sequence:ZFP
      sequence in control construct

<400> SEQUENCE: 13
```

```
Val Pro Gly Lys Lys Lys Gln His Ile Cys His Ile Gln Gly Cys Gly
 1               5                  10                  15

Lys Val Tyr Gly Gly His Asp Thr Val Gly His Leu Arg Trp His
             20                  25                  30

Thr Gly Glu Arg Pro Phe Met Cys Thr Trp Ser Tyr Cys Gly Lys Arg
         35                  40                  45

Phe Thr Ala Ala Asp Glu Val Gly Leu His Lys Arg Thr His Thr Gly
     50                  55                  60

Glu Lys Lys Phe Ala Cys Pro Glu Cys Pro Lys Arg Phe Met Leu Val
 65                  70                  75                  80

Val Ala Thr Gln Leu His Ile Lys Thr His Gln Asn Lys Lys Gly Gly
                 85                  90                  95

Ser

<210> SEQ ID NO 14
<211> LENGTH: 292
<212> TYPE: DNA
<213> ORGANISM: Artificial Sequence
<220> FEATURE:
<223> OTHER INFORMATION: Description of Artificial Sequence:designed
      ZFP construct (from KpnI to BamHI) targeting 9-base
      pair target site in VEGF promoter
<221> NAME/KEY: CDS
<222> LOCATION: (2)..(292)

<400> SEQUENCE: 14 g gta ccg ggc aag aag aag cag cac atc tgc cac atc cag ggc tgt ggt      49
  Val Pro Gly Lys Lys Lys Gln His Ile Cys His Ile Gln Gly Cys Gly
   1               5                  10                  15 aaa gtt tac ggc cgc tcc gac aac ctg acc cgc cac ctg cgc tgg cac        97
Lys Val Tyr Gly Arg Ser Asp Asn Leu Thr Arg His Leu Arg Trp His
             20                  25                  30 acc ggc gag agg cct ttc atg tgt aca tgg tcc tac tgt ggt aaa cgc       145
Thr Gly Glu Arg Pro Phe Met Cys Thr Trp Ser Tyr Cys Gly Lys Arg
         35                  40                  45 ttc acc aac cgc gac acc ctg gcc cgc cac aag cgt acc cac acc ggt       193
Phe Thr Asn Arg Asp Thr Leu Ala Arg His Lys Arg Thr His Thr Gly
     50                  55                  60 gag aag aaa ttt gct tgt ccg gaa tgt ccg aag cgc ttc atg cgc tcc       241
Glu Lys Lys Phe Ala Cys Pro Glu Cys Pro Lys Arg Phe Met Arg Ser
 65                  70                  75                  80 gac cac ctg tcc aag cac atc aag acc cac cag aac aag aag ggt gga       289
Asp His Leu Ser Lys His Ile Lys Thr His Gln Asn Lys Lys Gly Gly
                 85                  90                  95 tcc                                                                    292
Ser

<210> SEQ ID NO 15
<211> LENGTH: 97
<212> TYPE: PRT
<213> ORGANISM: Artificial Sequence
<220> FEATURE:
<223> OTHER INFORMATION: Description of Artificial Sequence:designed ZFP

<400> SEQUENCE: 15

Val Pro Gly Lys Lys Lys Gln His Ile Cys His Ile Gln Gly Cys Gly
 1               5                  10                  15

Lys Val Tyr Gly Arg Ser Asp Asn Leu Thr Arg His Leu Arg Trp His
             20                  25                  30

Thr Gly Glu Arg Pro Phe Met Cys Thr Trp Ser Tyr Cys Gly Lys Arg
         35                  40                  45
```

-continued

```
Phe Thr Asn Arg Asp Thr Leu Ala Arg His Lys Arg Thr His Thr Gly
         50                  55                  60

Glu Lys Lys Phe Ala Cys Pro Glu Cys Pro Lys Arg Phe Met Arg Ser
 65                  70                  75                  80

Asp His Leu Ser Lys His Ile Lys Thr His Gln Asn Lys Lys Gly Gly
                 85                  90                  95

Ser

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence:PCR primer
      hVEGFU1

<400> SEQUENCE: 16
gaattctgtg ccctcactcc cctgg                                          25

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence:PCR primer
      VEGFD2

<400> SEQUENCE: 17
accgcttacc ttggcatggt ggagg                                          25

<210> SEQ ID NO 18
<211> LENGTH: 25
<212> TYPE: DNA
<213> ORGANISM: Artificial Sequence
<220> FEATURE:
<223> OTHER INFORMATION: Description of Artificial Sequence:PCR primer
      hVEHFU2

<400> SEQUENCE: 18
acacaccttg ctgggtacca ccatg                                          25

<210> SEQ ID NO 19
<211> LENGTH: 26
<212> TYPE: DNA
<213> ORGANISM: Artificial Sequence
<220> FEATURE:
<223> OTHER INFORMATION: Description of Artificial Sequence:PCR primer
      VEGFD1

<400> SEQUENCE: 19
gcagaaagtc catggtttcg gaggcc                                         26

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence:PCR primer
      VEGFU2

<400> SEQUENCE: 20
tgtttagaag atgaaccgta agcct                                          25

<210> SEQ ID NO 21
```

```
<211> LENGTH: 25
<212> TYPE: DNA
<213> ORGANISM: Artificial Sequence
<220> FEATURE:
<223> OTHER INFORMATION: Description of Artificial Sequence:PCR primer
      VEGFD2

<400> SEQUENCE: 21
accgcttacc ttggcatggt ggagg                                        25

<210> SEQ ID NO 22
<211> LENGTH: 38
<212> TYPE: DNA
<213> ORGANISM: Artificial Sequence
<220> FEATURE:
<223> OTHER INFORMATION: Description of Artificial Sequence:PCR primer
      mVEGF

<400> SEQUENCE: 22
gcccccattg gtaccctggc ttcagttccc tggcaaca                          38

<210> SEQ ID NO 23
<211> LENGTH: 26
<212> TYPE: DNA
<213> ORGANISM: Artificial Sequence
<220> FEATURE:
<223> OTHER INFORMATION: Description of Artificial Sequence:PCR primer
      VEGFD

<400> SEQUENCE: 23
gcagaaagtc catggtttcg gaggcc                                       26
```